(12) United States Patent
Kuethe et al.

(10) Patent No.: US 7,544,815 B2
(45) Date of Patent: Jun. 9, 2009

(54) PROCESS FOR MAKING HYDROISOINDOLINE TACHYKININ RECEPTOR ANTAGONISTS

(75) Inventors: Jeffrey T. Kuethe, Somerset, NJ (US); Jingjun Yin, Green Brook, NJ (US); Mark A. Huffman, Warren, NJ (US); Michel Journet, Somerset, NJ (US)

(73) Assignee: Merck & Co, Inc., Rahway, NJ (US)

( * ) Notice: Subject to any disclaimer, the term of this patent is extended or adjusted under 35 U.S.C. 154(b) by 393 days.

(21) Appl. No.: 11/484,208

(22) Filed: Jul. 11, 2006

(65) Prior Publication Data

US 2007/0015923 A1 Jan. 18, 2007

Related U.S. Application Data

(60) Provisional application No. 60/698,761, filed on Jul. 13, 2005, provisional application No. 60/698,237, filed on Jul. 11, 2005.

(51) Int. Cl.
*C07D 209/44* (2006.01)

(52) U.S. Cl. ..................................... 548/512

(58) Field of Classification Search .................. 548/512
See application file for complete search history.

(56) References Cited

U.S. PATENT DOCUMENTS

| 7,217,731 | B2 * | 5/2007 | Bunda et al. | ............... 514/415 |
| 7,345,083 | B2 * | 3/2008 | Bunda et al. | ............... 514/415 |
| 2005/0165083 | A1 | 7/2005 | Bunda et al. | |

FOREIGN PATENT DOCUMENTS

WO           97/14671 A1      4/1997
WO     WO2005/073191      8/2005

OTHER PUBLICATIONS

Copending U.S. Appl. No. 11/922,446, U.S. National Stage Entry of PCT/US2006/026293.
International Search Report for International Application No. PCT/US2006/026293.
International Preliminary Report on Patentability for International Application No. PCT/US2006/026293.

* cited by examiner

*Primary Examiner*—Rebecca L Anderson
*Assistant Examiner*—Robert Havlin
(74) *Attorney, Agent, or Firm*—William Krovatin; Raynard Yuro

(57) ABSTRACT

The present invention is directed to a process for preparing certain hydroisoindoline compounds which are useful as neurokinin-1 (NK-1) receptor antagonists, and inhibitors of tachykinin and in particular substance P. The compounds are useful in the treatment of certain disorders, including emesis, urinary incontinence, depression, and anxiety.

13 Claims, No Drawings

PROCESS FOR MAKING HYDROISOINDOLINE TACHYKININ RECEPTOR ANTAGONISTS

CROSS REFERENCE TO RELATED APPLICATIONS

This application claims the benefit of Provisional Application Nos. 60/698,761, filed Jul. 13, 2005 and 60/698,237, filed Jul. 11, 2005.

BACKGROUND OF THE INVENTION

This application is directed to a process of making certain hydroisoindoline tachykinin receptor antagonists.

Substance P is a naturally occurring undecapeptide belonging to the tachykinin family of peptides, the latter being so-named because of their prompt contractile action on extravascular smooth muscle tissue. The tachykinins are distinguished by a conserved carboxyl-terminal sequence. In addition to substance P, the known mammalian tachykinins include neurokinin A and neurokinin B. The current nomenclature designates the receptors for substance P, neurokinin A, and neurokinin B as neurokinin-1 (NK-1), neurokinin-2 (NK-2), and neurokinin-3 (NK-3), respectively.

Tachykinin, and in particular substance P, antagonists are useful in the treatment of of clinical conditions which are characterized by the presence of an excess of tachykinin, in particular substance P, activity, including disorders of the central nervous system, nociception and pain, gastrointestinal disorders, disorders of bladder function and respiratory diseases.

An alternative process for making compounds of the same structural class is disclosed in PCT/US05/02149, filed Jan. 26, 2005. The process is discussed further hereinunder.

SUMMARY OF THE INVENTION

The present invention is directed to a process for preparing certain hydroisoindoline compounds which are useful as neurokinin-1 (NK-1) receptor antagonists, and inhibitors of tachykinin and in particular substance P. The compounds are useful in the treatment of certain disorders, including emesis, urinary incontinence, depression, and anxiety.

DETAILED DESCRIPTION OF THE INVENTION

In one aspect the invention encompasses a process of making hydroisoindoline tachykinin receptor antagonists of Formula (I)

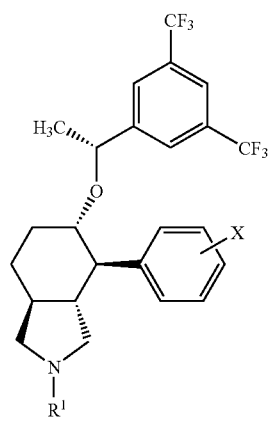

(I)

and pharmaceutically acceptable salts thereof, wherein
R1 is selected from the group consisting of
(1) hydrogen
(2) $C_{1-6}$alkyl, which is unsubstituted or substituted with halogen, hydroxyl or phenyl,
(3) cyclopentenone, which is unsubstituted or substituted with halogen, hydroxyl or methyl,
(4) —(CO)—$C_{1-6}$alkyl,
(5) —(CO)—$NH_2$,
(6) —(CO)—$NHC_{1-6}$alkyl, and
(7) —(CO)—$N(C_{1-6}$alkyl)($C_{1-6}$alkyl);
X is independently selected from the group consisting of:
(1) hydrogen,
(2) fluorine, and
(3) methyl;
comprising:
Step (a) reacting a phenyl acetic acid of Formula (2)

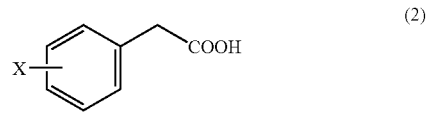

(2)

with $SOCl_2$ in an aprotic solvent optionally in the presence of a first catalyst to provide a compound of Formula (3)

(3)

Step (b) reacting the compound of Formula (3) with NHMeOMe in the presence of an aqueous inorganic base to provide a Weinreb amide of Formula (4)

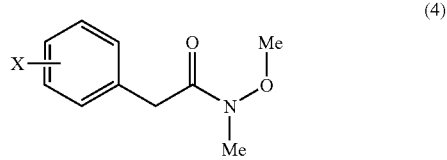

(4)

Step (c) reacting the Weinreb amid of Formula 4 with a suitable Grignard reagent in an second aprotic solvent followed by a first quenching with $Ac_2O$ and a second quenching with an aqueous inorganic acid to provide an enone of Formula (5)

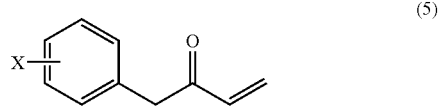

(5)

Step (d) reacting the enone of Formula (5) with a silane reagent in a third aprotic solvent and an organic base to provide a diene of Formula (6)

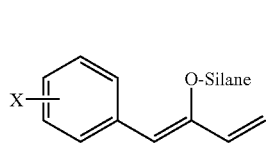

(6)

Step (e) reacting a diene of Formula (6) with a fumarate of Formula (7)

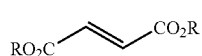

(7)

wherein R is (−)-menthyl and a Lewis acid in a non-polar solvent to provide a compound of Formula (8)

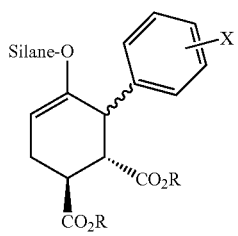

(8)

*Step (f) hydrolyzing a compound of Formula (8) with suitable hydrolysis reagents in an organic polar solvent to provide a compound of Formula (9)

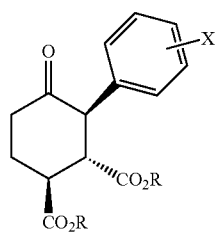

(9)

Step (g) reducing the ketone functionality of the compound of Formula (9) with a first reducing agent, followed by reduction of $CO_2R$ with a second reducing agent in an aprotic solvent to provide a triol of Formula (10)

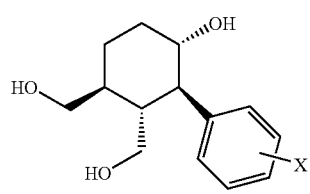

(10)

Step (h) reacting the triol of Formula (10) with an alkylsulfonyl chloride in the presence of an organic base to provide a compound of Formula (11)

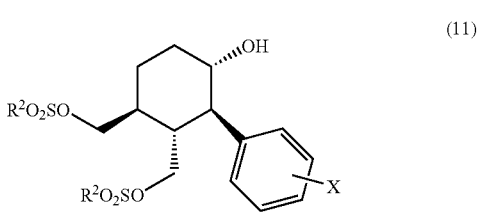

(11)

wherein $R^2$ is methyl, ethyl or propyl,

Step (i) reacting the compound of Formula (11) with compound of Formula (12)

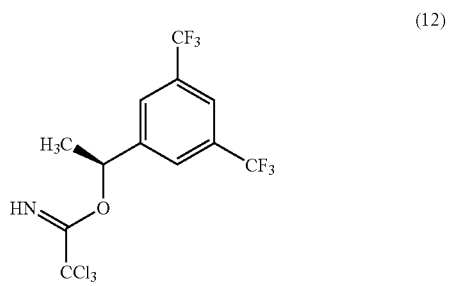

(12)

in the presence of an acid catalyst in an aprotic solvent to produce a compound of Formula (13)

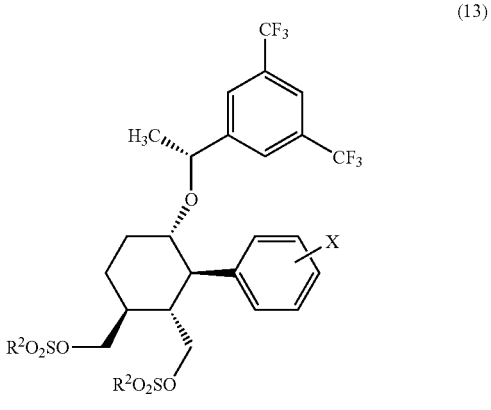

(13)

Step (j) cyclizing the compound of Formula (13) with allylamine in a polar solvent to provide a compound of Formula (14)

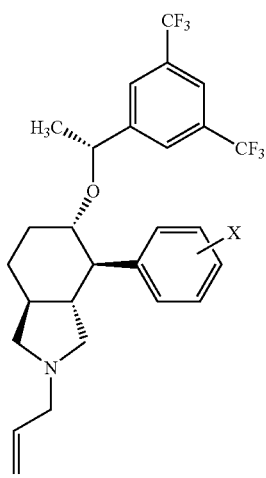

(14)

Step (k) reacting the compound of Formula (14) with third catalyst followed by addition of acid to provide a compound of Formula (15)

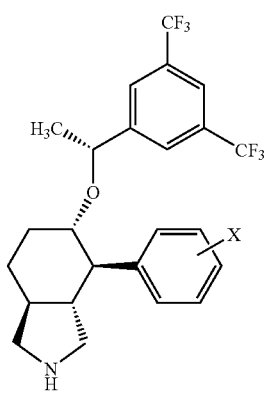

(15)

as an acid salt;

Step (l) reacting the acid salt of the compound of Formula (15) with a functionalizing reagent in a polar solvent to provide the compound of Formula (I)

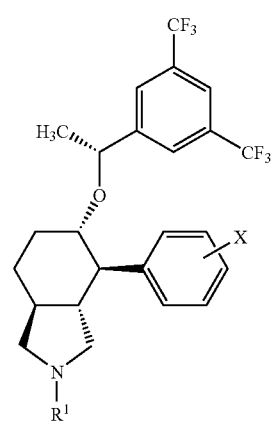

(I)

Regarding Step (a), the ratio of equivalents of (2) to $SOCl_2$ is typically 0.9:1 to 1:1.4. The preferred ratio is 1:1.2. For purposes of this application, the aprotic solvent includes toluene and benzene. Toluene is preferred. For purposes of this specification the first catalyst is defined to include Di-methylformamide. The ratio of molar equivalents of (2) to the first catalyst is 0.02. The reaction is typically carried out at a temperature range of 20 to 100° C. The preferred range is 60 to 80° C. The reaction is allowed to proceed until substantially complete, typically in 0.5 hours to 3 hours.

Regarding Step (b), the ratio of molar equivalents of (3) to NHMeOMe (as the HCl salt) is typically 1:1.2 to 1:2.0. The preferred ratio is 1:1.5. The reaction is typically carried out at a temperature range of −20 to 40° C. The preferred range is 0 to 20° C. The reaction is allowed to proceed until substantially complete, typically in 1 to 4 hours. In a preferred aspect Steps (a) and Step (b) is carried out in a single pot without intermediate isolation.

Regarding Step (c), the ratio of molar equivalents of (4) to Grignard reagent is typically 0.9:1.1 to 1.0:1.6. Preferably there is an excess of Grignard reagent, such as 20% to 40% excess. The Grignard reagents include vinyl magnesium or vinyl magnesium bromide. For purposes of this specification, the second aprotic solvent includes toluene, THF, Methyl-t-butyl ether (MTBE). The preferred solvent is a mixture of toluene and THF. The reaction is typically carried out at a temperature range of −78 to 0° C. The preferred range is −40 to −20° C. The reaction is quenched with 1.5 to 2 eq of acetic anhydride and then with an aqueous acidic buffer such as $NH_4Cl$ typically 0.5 to 2 hours after the reaction is begun.

Regarding Step (d), the molar ratio of (5) to silane reagent is typically 0.9:1 to 1:2.0. The preferred ratio is 1:1.6. Suitable silane reagents include chlorotriethylsilane, chlorotrimethylsilane, and t-butyldimethylchlorosilane. The preferred silane reagen is chlorotriethylsilane or chlorotrimethylsilane. The molar ratio of (5) to the organic base is typically 0.9:1 to 1:2.0. The preferred ratio is 1:1.6. Suitable organic base include triethylamine, ethyldiisopropylamine, and DBU. The preferred base is ethyldiisopropylamine. Suitable solvents include THF, MeCN, toluene, benzene, and ether. The preferred solvent is a mixture of MeCN, THF and toluene. The reaction is typically carried out at a temperature range of 0 to 30° C. The preferred range is 15-25° C. The reaction is allowed to proceed until substantially complete, typically in 16 to 30 hours.

Regarding Step (e), the molar ratio of (6) to (7) is typically 0.9:1 to 1:1.6. The preferred ratio is 1:1.2. The molar ratio of (6) to the Lewis acid catalyst is typically 1:1.2 to 1:3.0. The preferred ratio is 1:1.7. Suitable Lewis acid catalysts include $Et_2AlCl$, $iBu_2AlCl$, and $EtAlCl_2$. The preferred Lewis acid catalyst is $Et_2AlCl$. Suitable solvents include toluene, methylene chloride, 1,2-dichloroethane, and benzene. The preferred solvent is toluene. The reaction is typically carried out at a temperature range of −40 to 30° C. The preferred range is 0 to 20° C. The reaction is allowed to proceed until substantially complete, typically in 24 to 48 hours.

Regarding Step (f), the molar ratio of (8) to hydrolysis agent is typically 0.9:1 to 1:2.0. The preferred ratio is 1:1.2. Suitable hydrolysis agents include aqueous HCl, HBr, HF, and HI. The preferred hydrolysis agent is aqueous HCl. Suitable solvents include MeCN and THF. The preferred solvent is MeCN. The reaction is typically carried out at a temperature range of 0 to 40° C. The preferred range is 15 to 25° C. The reaction is allowed to proceed until substantially complete, typically in 1 to 4 hours.

Regarding Step (g), the molar ratio of (9) to the first reducing agent is typically 0.9:1 to 1:1.8. The preferred ratio is 1:1.5. Suitable first reducing agents include LiAl$(OtBu)_3$H and $NaBH_4$. The preferred first reducing agent is LiAl(OtBu)₃H. The molar ratio of (9) to the second reducing agent is typically 1:1.2 to 1:2.5. The preferred ratio is 1:1.3. Suitable second reducing agents include LiAlH₄ and LiBH₄. The preferred second reducing agent is LiAlH₄. Suitable solvents include THF and diglyme. The preferred solvent is THF. The reaction is typically carried out at a temperature range of –70 to 20° C. for the first reduction and –20 to 60 C for the second reduction. The preferred range is –40 to –25° C. for the first reduction and 20 to 40° C. for the second reduction. The reaction is allowed to proceed until substantially complete, typically in 1 to 5 hours for the first reduction and 2 to 18 hours for the second reduciton.

Regarding Step (h), the molar ratio of (10) to the alkanesulfonyl chloride is typically 1:2 to 1:3. The preferred ratio is 1:2.3 to 1:2.4. Suitable alkanesulfony chlorides include n-propanesulfonyl chloride, ethanesulfonyl chloride, and methanesulfonyl chloride. The preferred alkanesulfonyl chloride is n-propanesulfonyl chloride. The molar ratio of (10) to the organic base is typically 1:2 to 1:3. The preferred ratio is 1:2.3 to 1:2.4. Suitable organic bases include 2,4,6-collidine, ethyldiisopropylamine, tetramethylpiperidine, pentamethylpiperidine, 2,6-lutidine, and triethylamine. The preferred organic base is 2,4,6-collidine. Suitable solvents include MeCN, THF, methylene chloride, EtOAc, iPrOAc, 1,2-dichloroethane. The preferred solvent is a mixture of MeCN and EtOAc. The reaction is typically carried out at a temperature range of –20 to 40° C. The preferred range is 15 to 25° C. The reaction is allowed to proceed until substantially complete, typically in 3 to 20 hours.

Regarding Step (i), the molar ratio of (11) to (12) is typically 1.2:1 to 2.5:1. The preferred ratio is 1.4:1 to 1.6:1. The molar ratio of (11) to the acid catalyst is typically 1:0.05 to 1:0.40. The preferred ratio is 1:0.15 to 1:0.25. Suitable acid catalysts include HBF₄, BF₃, and CF₃SO₃H. The preferred acid catalyst is HBF₄. Suitable solvents include methylene chloride, 1,2-dichloroethane, toluene, trifluorotoluene, cyclohexane. The preferred solvent is a mixture of methylene chloride, cyclohexane and trifluorotoluene. The reaction is typically carried out at a temperature range of –20 to 20° C. The preferred range is –15 to –10° C. The reaction is allowed to proceed until substantially complete, typically in 15 to 24 hours.

Regarding Step (j), the molar ratio of (13) to allylamine is typically 1:5 to 1:10. The preferred ratio is 1:5. Suitable solvents include 2-propanol, MeOH, EtOH, i-PrOAc. The preferred solvent is 2-propanol. The reaction is typically carried out at a temperature range of 55-80° C. The preferred range is 55-60° C. The reaction is allowed to proceed until substantially complete, typically in 3 to 6 hours.

Regarding Step (k), the molar ratio of (14) to catalyst is typically 1:0.01 (1 mole %) to 1:0.05 (5 mole %). The preferred ratio is 1:0.01. The molar ratio of (14) to water is typically 1:4.5. The preferred ratio is 1:4.5. Suitable solvents include THF, MTBE. The preferred solvent is THF. The reaction is typically carried out at a temperature range of room temperature to 50° C. The preferred range is 40-45° C. The reaction is allowed to proceed until substantially complete, typically in 2 to 12 hours.

Regarding Step (l), the molar ratio of (15) to X' is typically 1:1.1 to 1:1.5. The preferred ratio is 1:1.1. Suitable solvents include 2-propanol, toluene. The preferred solvent is 2-propanol. The functionalizing agent includes, but is not limited to, an alkyl(aryl)halide, an alkyl(aryl)triflate, a dialkyl(aryl) carbonic anhydride, an acyl halide, an alkyl(aryl)chloroformate, alkyl(aryl)sulfonylhalide, a haloaklyl(aryl)sulfonylhalide, an alkanoyl halide, a benzylic halide, a halo-CON(alkyl or aryl)2, an alkyl(aryl)aldehyde or ketone in the presence of a reducing agent, a sulfonylate, for example a mesylate or tosylate. The reaction is typically carried out at a temperature range of room temperature to 110° C. The preferred range is 60 to 75° C. The reaction is allowed to proceed until substantially complete, typically in 1 to 3 hours.

Within this embodiment the process of the present invention includes compounds wherein R¹ is selected from the group consisting of:
(1) hydrogen,
(2) methyl,
(3) 2-phenylethyl,
(4) 2-hydroxyethyl,
(5) cyclopent-2-en-1-one,
(6) 5-hydroxycyclopent-2-en-1-one,
(7) 4-hydroxycyclopent-2-en-1-one,
(8) 2-methylcyclopent-2-en-1-one,
(9) acetyl,
(10) acetamido,
(11) methyl-acetamido, and
(12) dimethyl-acetamido.

Further within this embodiment, the present invention is directed to preparing compounds wherein R¹ is hydrogen.

Also further within this embodiment, the present invention is directed to preparing compounds wherein R¹ is methyl, 2-phenylethyl or 2-hydroxyethyl.

Also further within this embodiment, the present invention is directed to preparing compounds wherein R¹ is:

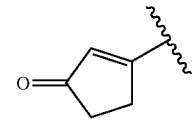

which is unsubstituted or substituted with hydroxyl or methyl.

Also further within this embodiment, the present invention is directed to preparing compounds wherein R¹ is acetyl, acetamido, methyl-acetamido or dimethyl-acetamido.

An embodiment of the present invention includes the preparation of compounds wherein X is hydrogen. An embodiment of the present invention includes compounds wherein X is fluorine. An embodiment of the present invention includes compounds wherein X is methyl.

Specific embodiments of the present invention includes the preparation of the compounds of the Examples herein and pharmaceutically acceptable salts thereof and individual enantiomers and diastereomers thereof.

The compounds of the present invention are useful in the prevention and treatment of a wide variety of clinical conditions which are characterized by the presence of an excess of tachykinin, in particular substance P, activity. Thus, for example, an excess of tachykinin, and in particular substance P, activity is implicated in a variety of disorders of the central nervous system. Such disorders include mood disorders, such as depression or more particularly depressive disorders, for example, single episodic or recurrent major depressive disorders and dysthymic disorders, or bipolar disorders, for example, bipolar I disorder, bipolar II disorder and cyclothymic disorder; anxiety disorders, such as panic disorder with or without agoraphobia, agoraphobia without history of panic disorder, specific phobias, for example, specific animal phobias, social phobias, obsessive-compulsive disorder, stress disorders including post-traumatic stress disorder and acute stress disorder, and generalised anxiety disorders; schizophrenia and other psychotic disorders, for example, schizophreniform disorders, schizoaffective disorders, delusional disorders, brief psychotic disorders, shared psychotic disorders and psychotic disorders with delusions or hallucinations; delerium, dementia, and amnestic and other cognitive or neurodegenerative disorders, such as Alzheimer's disease, senile dementia, dementia of the Alzheimer's type, vascular dementia, and other dementias, for example, due to HIV disease, head trauma, Parkinson's disease, Huntington's disease, Pick's disease, Creutzfeldt-Jakob disease, or due to multiple aetiologies; Parkinson's disease and other extra-pyramidal movement disorders such as medication-induced movement disorders, for example, neuroleptic-induced parkinsonism, neuroleptic malignant syndrome, neuroleptic-induced acute dystonia, neuroleptic-induced acute akathisia, neuroleptic-induced tardive dyskinesia and medication-induced postural tremour; substance-related disorders arising from the use of alcohol, amphetamines (or amphetamine-like substances) caffeine, cannabis, cocaine, hallucinogens, inhalants and aerosol propellants, nicotine, opioids, phenylglycidine derivatives, sedatives, hypnotics, and anxiolytics, which substance-related disorders include dependence and abuse, intoxication, withdrawal, intoxication delerium, withdrawal delerium, persisting dementia, psychotic disorders, mood disorders, anxiety disorders, sexual dysfunction and sleep disorders; epilepsy; Down's syndrome; demyelinating diseases such as MS and ALS and other neuropathological disorders such as peripheral neuropathy, for example diabetic and chemotherapy-induced neuropathy, and postherpetic neuralgia, trigeminal neuralgia, segmental or intercostal neuralgia and other neuralgias; and cerebral vascular disorders due to acute or chronic cerebrovascular damage such as cerebral infarction, subarachnoid haemorrhage or cerebral oedema.

Tachykinin, and in particular substance P, activity is also involved in nociception and pain. The compounds of the present invention will therefore be of use in the prevention or treatment of diseases and conditions in which pain predominates, including soft tissue and peripheral damage, such as acute trauma, osteoarthritis, rheumatoid arthritis, musculoskeletal pain, particularly after trauma, spinal pain, myofascial pain syndromes, headache, episiotomy pain, and burns; deep and visceral pain, such as heart pain, muscle pain, eye pain, orofacial pain, for example, odontalgia, abdominal pain, gynaecological pain, for example, dysmenorrhoea, and labour pain; pain associated with nerve and root damage, such as pain associated with peripheral nerve disorders, for example, nerve entrapment and brachial plexus avulsions, amputation, peripheral neuropathies, tic douloureux, atypical facial pain, nerve root damage, and arachnoiditis; pain associated with carcinoma, often referred to as cancer pain; central nervous system pain, such as pain due to spinal cord or brain stem damage; low back pain; sciatica; ankylosing spondylitis, gout; and scar pain.

Tachykinin, and in particular substance P, antagonists may also be of use in the treatment of respiratory diseases, particularly those associated with excess mucus secretion, such as chronic obstructive airways disease, bronchopneumonia, chronic bronchitis, cystic fibrosis and asthma, adult respiratory distress syndrome, and bronchospasm; inflammatory diseases such as inflammatory bowel disease, psoriasis, fibrositis, osteoarthritis, rheumatoid arthritis, pruritis and sunburn; allergies such as eczema and rhinitis; hypersensitivity disorders such as poison ivy; ophthalmic diseases such as conjunctivitis, vernal conjunctivitis, and the like; ophthalmic conditions associated with cell proliferation such as proliferative vitreoretinopathy; cutaneous diseases such as contact dermatitis, atopic dermatitis, urticaria, and other eczematoid dermatitis. Tachykinin, and in particular substance P, antagonists may also be of use in the treatment of neoplasms, including breast tumours, neuroganglioblastomas and small cell carcinomas such as small cell lung cancer.

Tachykinin, and in particular substance P, antagonists may also be of use in the treatment of gastrointestinal (GI) disorders, including inflammatory disorders and diseases of the GI tract such as gastritis, gastroduodenal ulcers, gastric carcinomas, gastric lymphomas, disorders associated with the neuronal control of viscera, ulcerative colitis, Crohn's disease, irritable bowel syndrome and emesis, including acute, delayed or anticipatory emesis such as emesis induced by chemotherapy, radiation, toxins, viral or bacterial infections, pregnancy, vestibular disorders, for example, motion sickness, vertigo, dizziness and Meniere's disease, surgery, migraine, variations in intercranial pressure, gastro-oesophageal reflux disease, acid indigestion, over indulgence in food or drink, acid stomach, waterbrash or regurgitation, heartburn, for example, episodic, nocturnal or meal-induced heartburn, and dyspepsia.

Tachykinin, and in particular substance P, antagonists may also be of use in the treatment of a variety of other conditions including stress related somatic disorders; reflex sympathetic dystrophy such as shoulder/hand syndrome; adverse immunological reactions such as rejection of transplanted tissues and disorders related to immune enhancement or suppression such as systemic lupus erythematosus; plasma extravasation resulting from cytokine chemotherapy, disorders of bladder function such as cystitis, bladder detrusor hyper-reflexia, frequent urination and urinary incontinence, including the prevention or treatment of overactive bladder with symptoms of urge urinary incontinence, urgency, and frequency; fibrosing and collagen diseases such as scleroderma and eosinophilic fascioliasis; disorders of blood flow caused by vasodilation and vasospastic diseases such as angina, vascular headache, migraine and Reynaud's disease; and pain or nociception attributable to or associated with any of the foregoing conditions, especially the transmission of pain in migraine. The compounds of the present invention are also of value in the treatment of a combination of the above conditions, in particular in the treatment of combined post-operative pain and post-operative nausea and vomiting.

The compounds of the present invention are particularly useful in the prevention or treatment of emesis, including acute, delayed or anticipatory emesis, such as emesis induced by chemotherapy, radiation, toxins, pregnancy, vestibular disorders, motion, surgery, migraine, and variations in intercranial pressure. For example, the compounds of the present invention are of use optionally in combination with other antiemetic agents for the prevention of acute and delayed nausea and vomiting associated with initial and repeat courses of moderate or highly emetogenic cancer chemotherapy, including high-dose cisplatin. Most especially, the compounds of the present invention are of use in the treatment of emesis induced by antineoplastic (cytotoxic) agents, including those routinely used in cancer chemotherapy, and emesis induced by other pharmacological agents, for example, rolipram. Examples of such chemotherapeutic agents include alkylating agents, for example, ethyleneimine compounds, alkyl sulphonates and other compounds with an alkylating action such as nitrosoureas, cisplatin and dacarbazine; antimetabolites, for example, folic acid, purine or pyrimidine antagonists; mitotic inhibitors, for example, vinca alkaloids and derivatives of podophyllotoxin; and cytotoxic antibiotics. Particular examples of chemotherapeutic agents are described, for instance, by D. J. Stewart in *Nausea and Vomiting: Recent Research and Clinical Advances*, Eds. J.

Kucharczyk et al, CRC Press Inc., Boca Raton, Fla., USA (1991) pages 177-203, especially page 188. Commonly used chemotherapeutic agents include cisplatin, dacarbazine (DTIC), dactinomycin, mechlorethamine, streptozocin, cyclophosphamide, carmustine (BCNU), lomustine (CCNU), doxorubicin (adriamycin), daunorubicin, procarbazine, mitomycin, cytarabine, etoposide, methotrexate, 5-fluorouracil, vinblastine, vincristine, bleomycin and chlorambucil [R. J. Gralla et al in *Cancer Treatment Reports* (1984) 68(1), 163-172]. A further aspect of the present invention comprises the use of a compound of the present invention for achieving a chronobiologic (circadian rhythm phase-shifting) effect and alleviating circadian rhythm disorders in a mammal. The present invention is further directed to the use of a compound of the present invention for blocking the phase-shifting effects of light in a mammal.

An alternative process for making compounds of the same class is disclosed in PCT/US05/02149, filed Jan. 26, 2005. Referring specifically to Example 7, the process can be summarized as shown in the scheme immediately below. Significant disadvantages are that the route is racemic and requires the chromatographic separation of both enantiomers and diastereomers after the reduction of racemic ketone IV. In addition, the synthesis requires 5 steps to bismesylate VIII from ketone IV (reduction, separation, etherification, reduction, mesylation). This route utilized a benzyl-protecting group of the octahydroisoindole. Removal of this group by palladium-catalyzed hydrogenation was followed by reaction with 1,3-cyclopentanedione to give the product of Example 7.

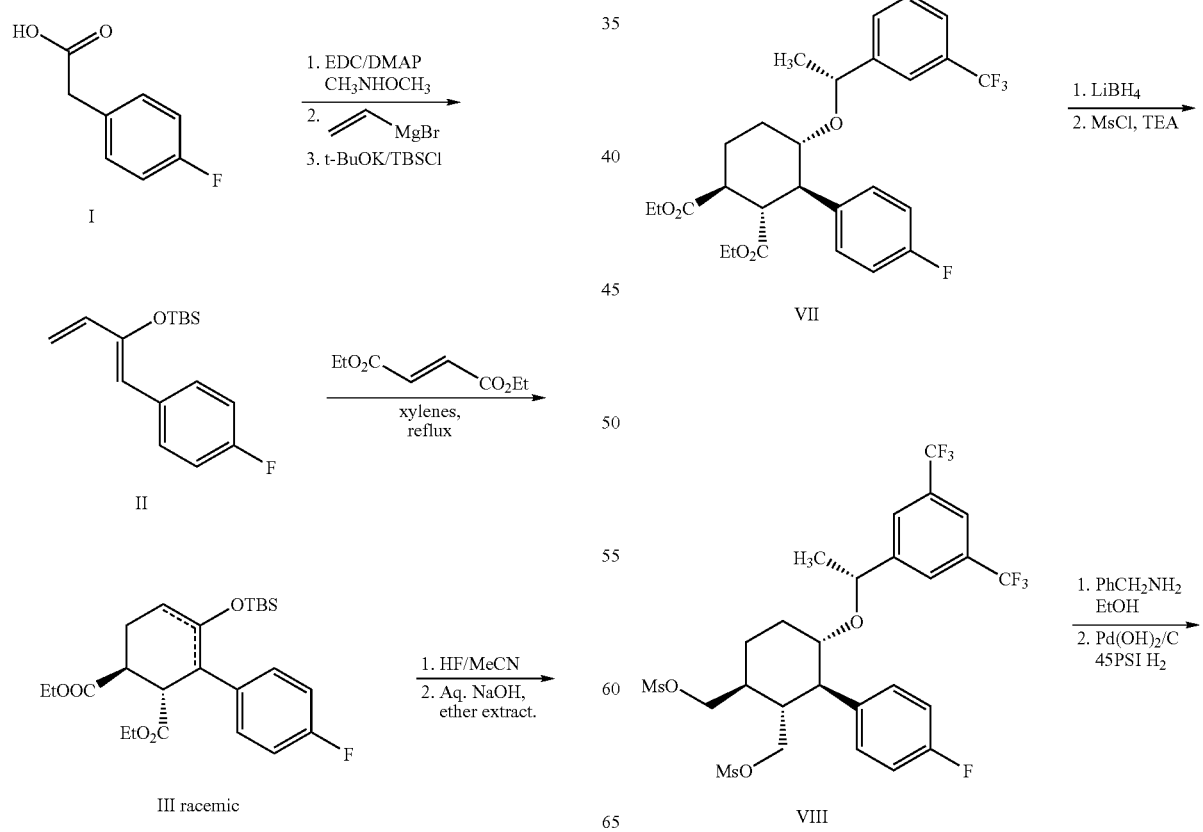

13

-continued

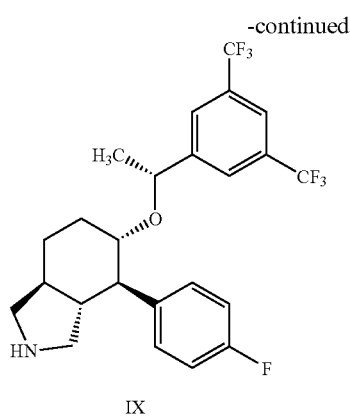

IX

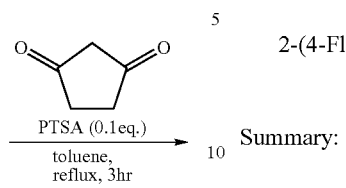

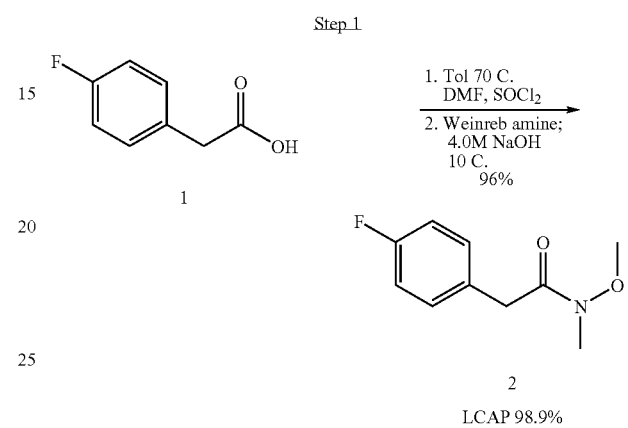

Example 7

14

EXAMPLE 1

Process to Ketone

Step 1:
2-(4-Fluorophenyl)-N-methoxy-N-methylacetamide
(2)

Summary:

Step 1

1. Tol 70 C.
   DMF, SOCl₂
2. Weinreb amine;
   4.0M NaOH
   10 C.
   96%

2

LCAP 98.9%
LCWP 99.0%

This reaction gives consistently high yield and high purity of material. No major side products have been identified. The final product is an oil (typically clear or slightly yellow) and is isolated with the above purity profile from the crude work up.

Procedure:

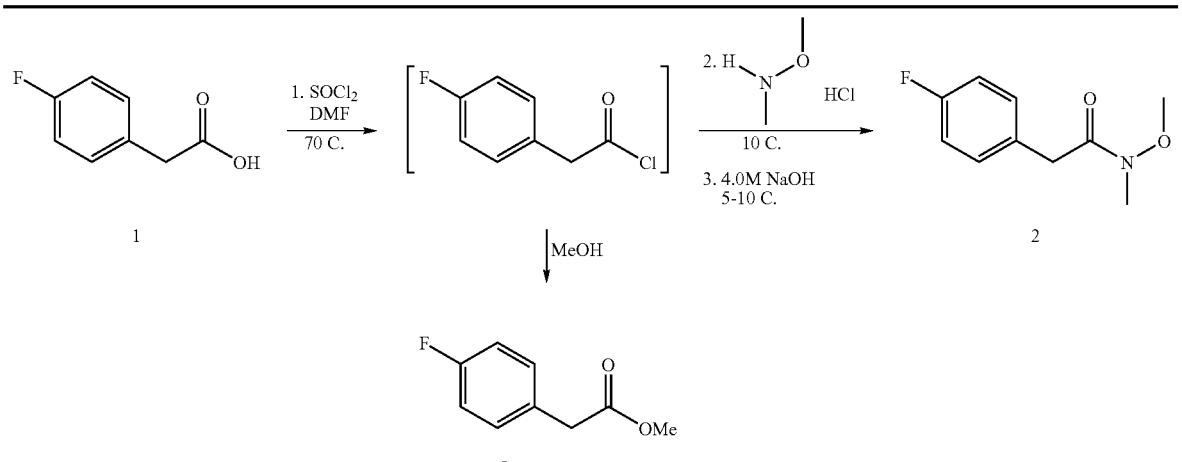

| | FW: | Amt. | Moles | Equiv. |
|---|---|---|---|---|
| 4-Fluorophenylacetic acid (1) | 154 | 5.0 kg | 32.47 mol | 1.0 eq. |
| DMF | 73.1 | 48 mL | 0.65 mol | 0.02 eq. |
| SOCl₂ | 119 | 2.84 L | 38.96 mol | 1.2 eq. |
| Weinreb amine-HCl | 97.5 | 4.75 kg | 48.70 mol | 1.5 eq. |
| NaOH | 4.0 M | 32.47 L | 129.87 mol | 4.0 eq. |
| Toluene | — | 49.19 L | — | |
| Brine | — | 64.92 L | — | |

A 100 L extractor equipped with a reflux condenser, and a base scrubber was charged with toluene (49.2 L, KF≦100 ppm) and 4-fluorophenylacetic acid (1) was added (5.0 kg). This solution was heated to 70° C. Once 70° C. was reached the DMF (48 mL, KF≦150 ppm) was added and thionyl chloride (2.8 L) was slowly added over 3 hours.

Batch temperature will decrease while thionyl chloride is added. Typical temperature changes range from 6-10° C.

When all thionyl chloride has been added and off-gassing has ceased (typically 30 min. after addition is complete) an aliquot of the batch was quenched into excess methanol for HPLC analysis as the methyl ester.

Reaction is done when acid 1 is at <0.5 LCAP.

Next the reaction was cooled to 5-10° C. The Weinreb amine-HCl (4.75 kg) was added to the batch at this point. Slow addition of NaOH (32.5 L) was begun at this point. This base was added at a rate that maintained the batch temperature at or below 10° C. with a typical addition time of 3 hours. Once this addition was done an aliquot of the batch was quenched into MeOH and assayed by HPLC to check for complete consumption of the acid chloride.

Complete consumption of the acid chloride (in the form of the methyl ester after this quench) should be seen. Additional base can be added if the acid chloride is still present.

The biphasic solution was separated at between 5° C. and room temperature and the organic phase was washed with 15 wt. % NaCl (aq) (2×32.5 L).

Typical assay yield of the organic phase was 96%.

The organic phase was concentrated to a 50 wt. % solution (typical KF≦500 ppm).

Step 2: 1-(4-Fluorophenyl)but-3-en-2-one (3)

Summary:

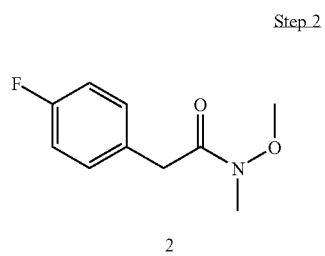

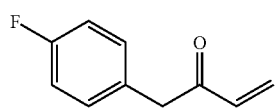

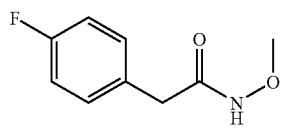

A

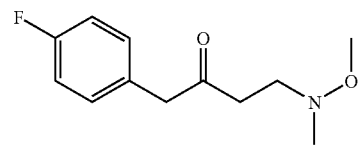

B

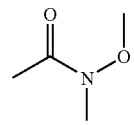

C

This reaction is very sensitive to the quality of the Grignard reagent and the quench method. Major side products have been identified (A, B, C), and are shown above. The product is unstable when concentrated to an oil, and has moderate stability in solution. The final toluene solution should be kept cold and used in the next step without delay.

Procedure:

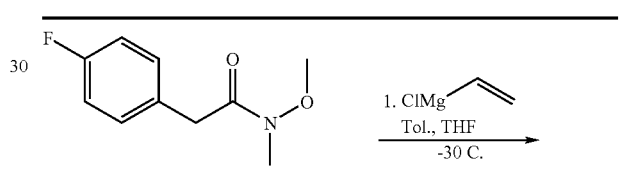

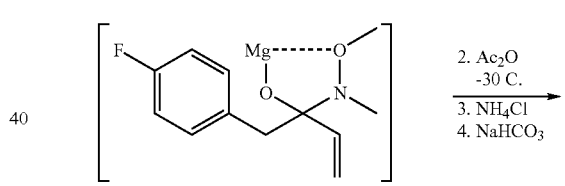

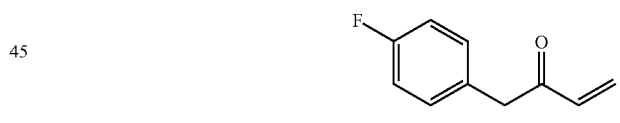

| | FW: | Amt. | Moles | Equiv. |
|---|---|---|---|---|
| Weinreb amide (2) | 197.2 | 157.2 g | 0.800 mol | 1.0 eq. |
| Vinyl magnesium chloride in THF | 1.6 M | 700 mL | 1.12 mol | 1.4 eq. |
| Ac₂O (density 1.082 g/mL) | 102 | 151 mL | 1.60 mol | 2.0 eq. NH₄Cl |
| (2.5 wt % aq. solution) | — | 1.29 L | — | — |
| Toluene (density 0.865 g/mL) | — | 1.54 L | — | — |

A 3 L round bottom flask equipped with an addition funnel was charged with the Weinreb amide 2 as a 61% wt solution in toluene (262 g tot mass; 157.2 g 2, 105 g toluene). This solution was diluted to a 0.5 M solution of amide 2 in toluene by addition of 1.32 L of toluene (KF of solution≦150 ppm). This solution was cooled to −30° C., and vinyl magnesium chloride was slowly added.

During the addition of vinyl magnesium chloride the batch temperature is maintained at −30° C. Typical addition time is around 60 minutes.

After the vinyl Grignard addition was complete the reaction was allowed to age at −30° C. for 60 minutes. The reaction was checked by HPLC after this 60 minute age.

Acetic anhydride (151 mL) was then slowly added to the reaction.

Batch temperature is maintained at −30° C. during this addition to avoid impurities. Typical time is 30 minutes. Assay of the reaction at the end of this addition typically shows approximately 0.5% LCAP of impurity B when compared to product.

In a separate 5 L 3-neck round bottom flask a 2.5 wt % solution of NH$_4$Cl in water (1.29 L) was cooled to 10° C. The batch at −30° C. was cannulated to this vigorously stirred ammonium chloride solution.

The final temperature of the batch is typically around 12-13° C.

When the batch had reached ambient temperature the aqueous and organic layers were cut. The organic layer was then washed with water (1.3 L). The organic layer was dried with MgSO$_4$ powder (~100-200 g) until the KF of this solution reached at or below 1000 ppm. The solids were filtered away and washed with dry MeCN (4×50 mL) to provide a solution of the product in THF/MeCN/Toluene (~2.0 L, KF ~970 ppm, 1.80 kg, 7.29 wt %, 131 g of 3, 100% yield) which was used directly in the next step.

The impurity profile shows 1.5 LCAP of impurity B and 9.1 LCAP of impurity C.

Step 3: TES dienyl ether

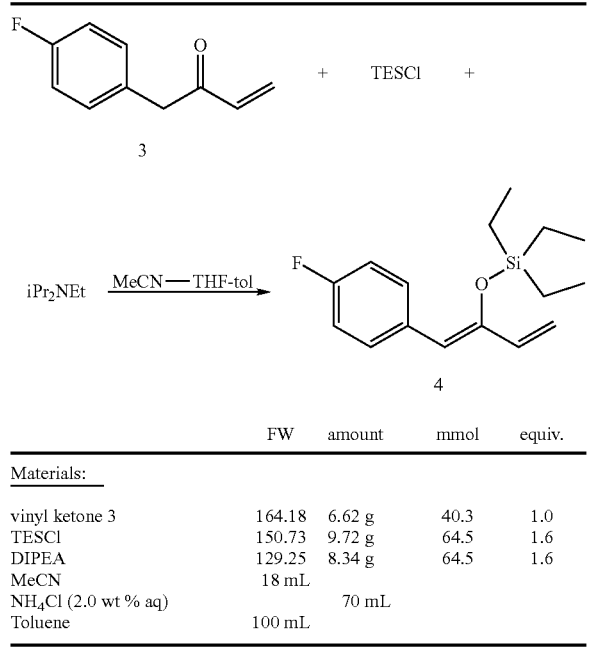

| Materials: | FW | amount | mmol | equiv. |
|---|---|---|---|---|
| vinyl ketone 3 | 164.18 | 6.62 g | 40.3 | 1.0 |
| TESCl | 150.73 | 9.72 g | 64.5 | 1.6 |
| DIPEA | 129.25 | 8.34 g | 64.5 | 1.6 |
| MeCN | | 18 mL | | |
| NH$_4$Cl (2.0 wt % aq) | | 70 mL | | |
| Toluene | | 100 mL | | |

Procedure:

To 90.8 g of the 7.29 wt % enone 3 solution in THF/MeCN/toluene obtained from step 2 at rt was added more dry MeCN (18 mL) and iPr$_2$NEt. TESCl was then added slowly while maintaining rt. The solution was stirred at rt until LC revealed complete conversion (~16 h).

The reaction was quenched with 2 wt % aq NH$_4$Cl (70 mL). The organic layer was separated and washed with water (70 mL). It was then concentrated and flushed with toluene to ~37 wt % with a KF of ~200 ppm. Assay yield: 8.64 g, 77%. NMR shows <5% of the E-isomer.

Step 4: Di-(−)-menthylfumarate

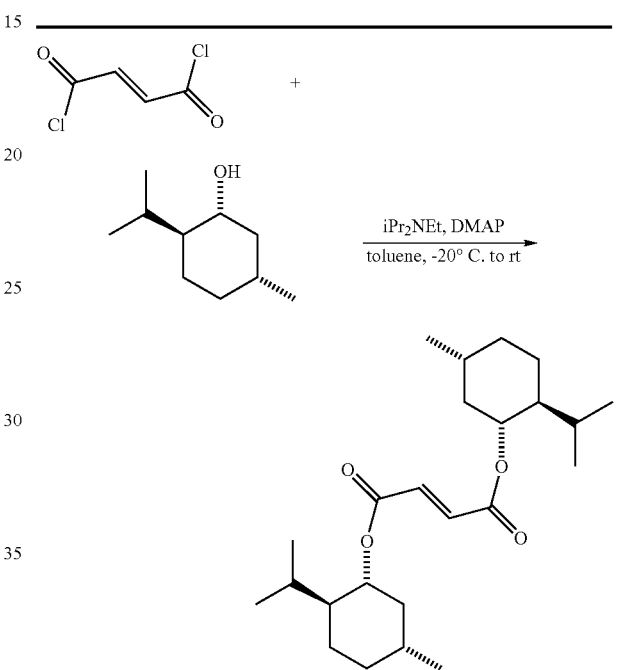

| | FW | d/conc | amount | mol | equiv. |
|---|---|---|---|---|---|
| Materials: | | | | | |
| fumaryl chloride | 152.96 | 1.412 | 80.5 g (95%) | 0.50 | 1.0 |
| (1R, 2S, 5R)-(−)-menthol | 156.27 | | 157.8 g | 1.01 | 2.02 |
| i-Pr$_2$NEt | 129.25 | 0.742 | 191 mL | 1.10 | 2.20 |
| DMAP | 122.17 | | 3.05 g | 0.025 | 0.05 |
| toluene | | | 600 mL | | |
| 1.0 N HCl | | | 110 mL | 0.11 | 0.22 |
| NaCl | | | 60 g | | |

Procedure:

To a 3-neck flask was charged toluene (500 mL) and (−)-menthol (157.8 g). The solution was cooled to −20° C. and fumaryl chloride (80.5 g of 95%) was charged with 80 mL toluene flush (no exotherm was observed). i-Pr$_2$NEt (191 mL) was added over 30 min (fuming) with 20 mL toluene flush at −20° C. DMAP was added immediately afterwards. The dark slurry was then allowed to warm to 21° C. over ~60 min to give a dark solution, which showed complete conversion by HPLC.

At room temperature, a mild exotherm caused the temperature to rise to ~30° C. It will be desirable to age at −20 to 0° C. for 1-2 h before warming up to rt.

600 mL of aqueous 3% NaCl was added. The aqueous layer (~800 mL) was cut away and the organic layer was washed with 800 mL aqueous 0.15 N HCl containing 5 wt % NaCl. The dark organic layer (~800 mL, 710 g) showed 93% assay yield (182 g, 0.464 mol product in 98LCAP) and was concentrated to 378 g (48 wt %) for direct use in the Diels-Alder reaction. $^1$H NMR showed non-detectable menthol.

Step 5: Diels-Alder

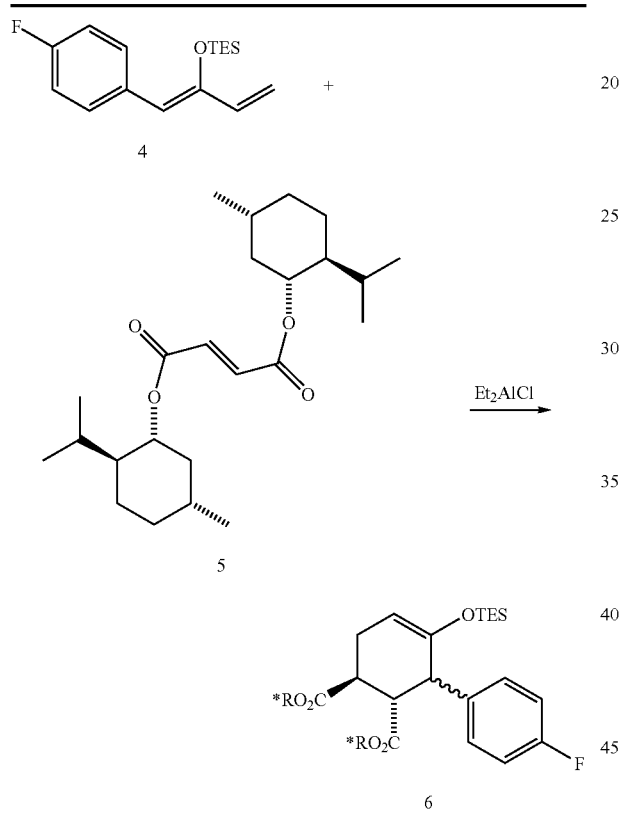

| | FW | amount | mmol | equiv. |
|---|---|---|---|---|
| Materials: | | | | |
| diene 4 | 278.44 | 8.64 g | 31 | 1.0 |
| di-(−)-menthyl fumarate 5 | 392.57 | 14.6 g | 37.2 | 1.2 |
| diethylaluminum chloride | 1.8 M/tol | 29.3 mL | 52.7 | 1.7 |
| hydrochloric acid | 3.0 N | 52.7 mL | 158.1 | 5.1 |
| hydrochloric acid | 1.0 N | 100 mL | 100 | 3.2 |
| NaOH | 0.5 N | 50 mL | 25 | 0.81 |

Procedure:

The toluene solutions of diene 4 (23.4 g, 37 wt %) and dimenthylfumarate 5 (30.4 g, 48 wt %) were combined and cooled to 0° C. Diethylaluminum chloride solution in toluene (1.8M, 29.3 mL) was added over 45 min, keeping the temperature below 5° C. (exothermic addition). The dark orange solution was aged at 0° C. for 18 h (~90% conversion), and then at 21° C. for 6 h when it reached >95% conversion.

If the desired conversion was not achieved, more Lewis acid (and dimenthyl fumarate if necessary) could be added at any point of the reaction.

The reaction mixture was carefully quenched with aqueous 3 N HCl (8 mL) over >60min while keeping the temperature at 15-25° C.

It is important to add this first portion of HCl very slowly without any bursts. Although the batch is not very sensitive to heat, rapid off-gassing and foaming upon addition of HCl could result in a disastrous overflow of the batch. The foaming needs to be watched very closely.

The remaining HCl (3N, 44.7 mL) was added slowly while keeping temperature at 15-25° C., and the resulting mixture was aged for 30 min at rt. The aqueous layer was removed, and the organic layer was washed with 1 N aq HCl (2×50 mL) and 0.5 N aq NaOH (50 mL). The toluene solution was used directly in the next step Any E-isomer of the diene (<5%) which is present does not react in the Diels-Alder reaction.

A small amount of deprotected products 7 could form in the organic layer during the work-up.

Step 6: Deprotection and Epimerization

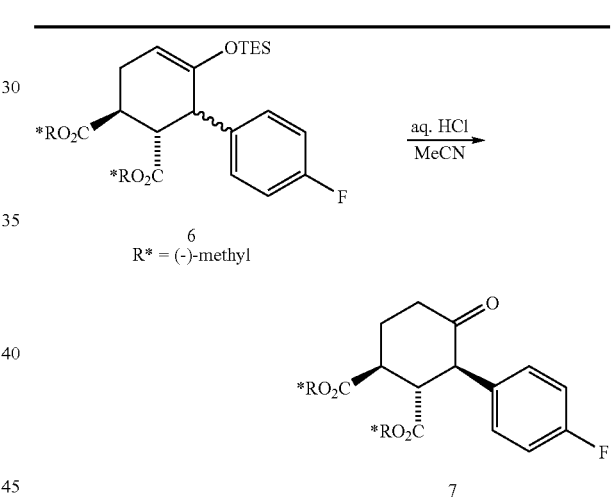

| | FW | amount | mmol | equiv. |
|---|---|---|---|---|
| Materials: | | | | |
| cyclohexene 6 | 671.01 | | 31 | 1.0 |
| acetonitrile | | 211 mL | | |
| aqueous 6.0 N HCl | | 6.2 mL | 37.3 | 1.2 |

Procedure:

The toluene solution from step 5 was concentrated to remove all solvents, flushed with acetonitrile, to give 210 mL slurry in acetonitrile. Aqueous 6 N HCl (6.2 mL) was added. The slurry was stirred at room temperature for ~2 h, at which point HPLC indicated that the reaction was complete.

The desilylation initially gave a mixture of 2,3-cis and 2,3-trans ketones, which, driven by crystallization of desired 7, isomerized to predominantly trans.

After aging, filtration followed by 3×51.4 mL (3.5 volumes) acetonitrile slurry washes and drying in vacuo overnight at 60° C. yields a white solid (15.3 g, 98.6 wt %, 87% yield).

EXAMPLE 2

Ketone Reduction to Compound A

Step 1. Ketone Reduction to Triol

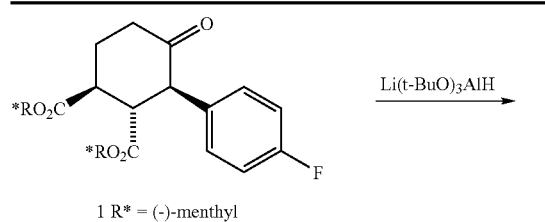

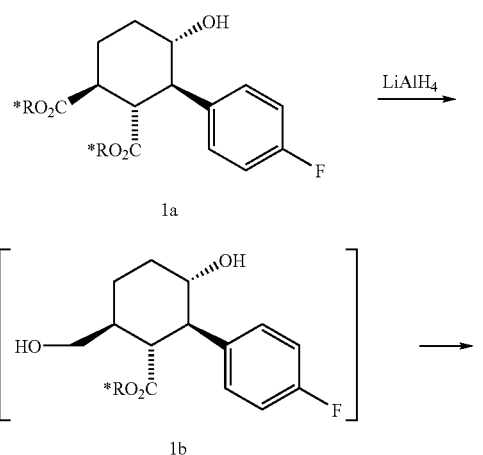

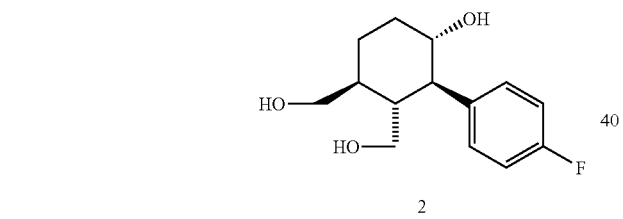

| | FW | mass | volume | mol | equiv. |
|---|---|---|---|---|---|
| Materials: | | | | | |
| ketone 1 | 556.75 | 7.25 kg (96.5 wt %) | | 12.57 | 1 |
| Li(t-BuO)₃AlH THF | (KF = 74.5 ppm) | (1.0 M THF) | 18.9 L 25 L | 18.86 | 1.5 |
| LiAlH₄ | (2.3 M THF) | | 7.11 L | 16.34 | 1.3 |
| HCl | (50% v/v, 6.0 N) | | 29.5 L | 177 | 14.1 |
| HCl | (conc., 12 N) | | 8.9 L | 106.8 | 8.5 |
| Heptane | | | 35 L | | |
| NaOH | (10.0 N) | | 14 L | 140 | 11.1 |
| Ethyl Acetate | | | 2 × 39 L | | |
| 2,4,6-collidine | 121.18 | 0.064 kg | 2 × 0.035 L | 2 × 0.25 | 0.04 |

Procedure

Add 22 L THF to a 100 L RBF with an inert atmosphere. Cool the flask to −40° C. and add Li(O-tBu)₃AlH. Charge ketone 1 as a solid with a THF (3 L) rinse while keeping temp<−25° C. Stir at −30 to −35° C. until <5% starting material remains (all solid dissolves), approximately 2-3 hours. The trans/cis ratio is typically ~25.

Warm the reaction mixture to ~−20° C. and add LiAlH₄. Allow the batch warm up to ~−10° C. and apply cooling to keep the temperature<30° C. Stir the reaction mixture at room temperature until observing complete reduction to the triol (<0.5% desired diol 1b left), >3 hours.

Cool the batch to ~0° C. and reverse quench slowly into 6.0 N HCl (23.5 L) while keeping the temperature<40° C. Use 2 L THF to rinse the reaction vessel. Caution! Significant H₂ off-gassing and exotherm will occur over the entirety. Two clear layers should form if settling occurs. Concentrate the quenched solution to ~30 L (4.3V) (water starts to condense at this point).

Add heptane (35 L) followed by 6.0 L 6.0 N HCl and 8.9 L 12.0N HCl to dissolve a rag layer. Cut and keep the aqueous layer (~40 L) (org layer ~43 L), being certain to keep any rag (<250 mL) with the aqueous. Assay each layer to ascertain the menthol distribution, which should show<2% remaining in the aqueous. Charge the aq layer back to the extractor with 1 L water rinse. Titrate to pH ~1.5-2 with ~14 L 10N NaOH while keeping temperature<30° C. (charge 12 L first, followed by 0.5 L portions; pH is ~0 after 13 L is charged; it could take ~10-15 min for pH meter to give a stable pH reading.).

Add 39 L EtOAc and stir vigorously for 30 min. Make sure pH is ~1.5-2, otherwise add 10 N NaOH or conc HCl in 250 mL portions to adjust the pH. Allow 1-2 h for the emulsion layer to break up. Cut and keep the aqueous (50 L), which should show ~14% product remaining. Drum off the organic (41 L) followed by addition of collidine (35 mL) to adjust to pH ~4-4.5. Repeat the extraction once more with 39 L EtOAc (faster settling this time). The aqueous layer should show ~2% product remaining and is discarded.

A pH of −0.4 would result in slow decomposition of the triol, possible to acetate at ~0.1%/h. A higher pH to ~1.8-2.0 reduces the aq solubility of triol, but too high a pH would result in gel formation (Al(OH)₃?). The triol solution in EtOAc is stable at pH 1.4-5 at rt and at pH 4-5 at 45° C. (8 days).

Concentrate the combined organic layers and flush with EtOAc to ~9 L with a KF<1000 ppm. Drum off with an inline filter with 3 L MeCN rinse. Expected yield: 2.91 kg of trans-triol (91%Y), 3.02 kg total triols (trans/cis ~25). The resulting solution is stable at rt for >9 days and at 50° C. for >4 days.

Step 2: Sulfonylation

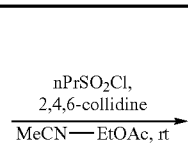

-continued

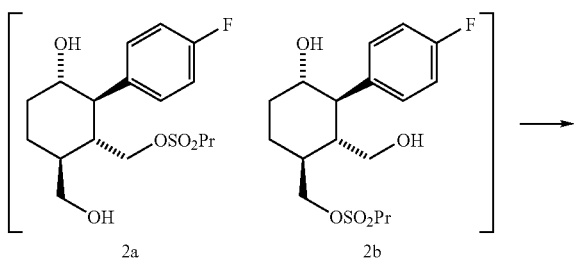

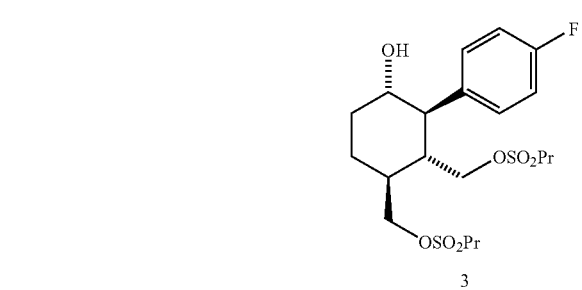

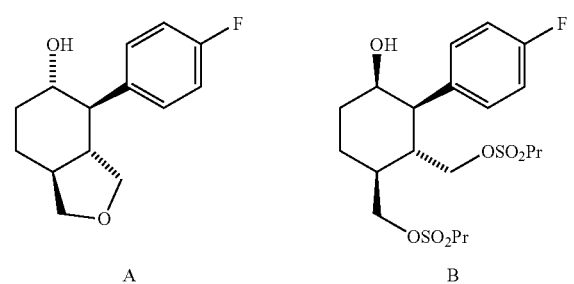

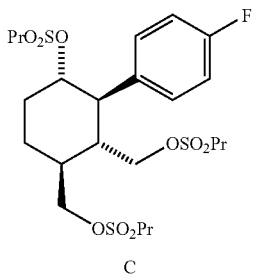

| | FW | mass | volume | mol | equiv. |
|---|---|---|---|---|---|
| Materials: | | | | | |
| Triol 2 | 254.30 | 4.34 kg | | 17.1 | 1.0 |
| nPrSO$_2$Cl | 142.6 | 6.59 kg | 5.18 L | 46.2 | 2.7 |
| collidine | 121.18 | 6.01 kg | 6.55 L | 49.6 | 2.9 |
| MeCN | | | 22 L | | |
| HCl | (1.0 N) | | 21.6 L | 21.6 | 1.26 |
| EtOAc | | | 14 L | | |
| NaCl | 10% aq | | 38 L | | |
| HCl | (50% v/v) | | 0.50 L | 3 | 0.018 |
| NaOH | (1.0 N) | | 30 L | 30 | 1.75 |
| NaCl | 6% aq | | 20 L | | |

Procedure

Charge the triol solution (containing 4.34 kg active triol+ 0.23 kg of other triols and ~8.7 L EtOAc+4 L MeCN, KF ~2000ppm, equiv 10 mol % H$_2$O), MeCN (14 L) and n-PrSO$_2$Cl to a 100 L extractor. Cool the solution to 15° C. and add collidine all in one portion. Apply cooling to keep the reaction temperature at 18-21° C. A slurry forms within 30 min.

Monitor the reaction by LC every hour after 2 h mark until no starting material and <2.5% of the mono-sulfonates 2a+b are left (typically 4-6 hours). Leaving the reaction run for longer leads to more tri-sulfonate C formation.

After 230 min (2a+b: 120 min-14.4 A %, 180 min-4.6 A %, 210min-1.4 A %, non-SM related peaks-collidine, EtOAc, n-PrSO$_2$Cl-are not integrated), quench the reaction with 1 N HCl (21.6 L) and add 14 L more EtOAc The quench is slightly endothermic to ~15° C. and then back to ~18° C. Cut away the bottom aqueous layer (~34 L). Wash the organic layer with 10% NaCl (38 L) combined with 50% v/v HCl (6.0 N, 0.50 L) to remove any residual collidine. Cut away the bottom aq layer (~41 L) and add NaOH (1 N, 30 L, removing PrSO$_2$Cl) to the organic layer while keeping temperature<27° C. Stir for 15 min and let the layers settle. Cut away the aq layer (~36 L) and wash the organic layer, which should show<2 mol % of n-PrSO$_2$Cl left, with 6% NaCl (20 L). Cut away the aq layer (~24 L ) and collect the organic layer (25.6 kg) with 1 L EtOAc rinse and assay for yield (6.80 kg 3, 85%).

It is then concentrated to an oil, flushed with 20 L cyclohexane to an oil and then with 30 L CH$_2$Cl$_2$ to ~10 L (transfer the solution to a new flask via an inline filter after 15 L CH$_2$Cl$_2$ is used and then continue the distillation), when KF should be <250 ppm and EtOAc <8 mol % by LC.

The solution is used for the next reaction.

Step 3: Imidate Preparation

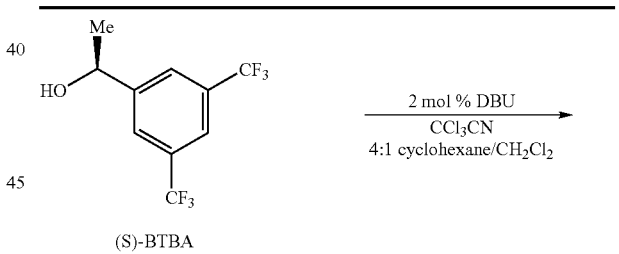

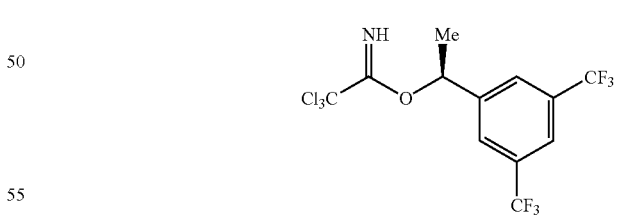

| | FW | mass | volume | mol | equiv. |
|---|---|---|---|---|---|
| Materials: | | | | | |
| (S)-BTBA | 258.16 | 8.00 kg | | 31.0 | 1.0 |
| CCl3CN | 144.4 | 4.92 kg | 3.42 L | 34.07 | 1.1 |
| DBU | 152.24 | | 92.2 mL | 0.62 | 0.02 |
| Cyclohexane | | | 42.4 L | | |
| CH$_2$Cl$_2$ | | | 8.6 L | | |

Procedure:

To a 100 Liter Flask containing 27 L of a 4:1 mixture of cyclohexane/CH₂Cl₂ was added 8.0 Kg of (S)-BTBA as a solid and the sides of the flask were rinsed with an additional 10.3 L of 4:1 mixture of cyclohexane/CH₂Cl₂. To the resulting slurry was added 4.92 Kg (3.42 Liters) of trichloroacetonitrile followed by 92.2 mL of DBU. The reaction mixture was aged at rt for 5.5 h and assayed for completion. The reaction mixture was then transferred to a 100 Liter extractor rinsing the reaction flask with cyclohexane. The mixture was washed with 27 Liters of water and then with 27 liters of brine. The organic layer was then filtered over a small plug of Solka floc and azetropically distilled under reduced pressure (24 mmHg, internal temp<35° C.) and a final volume of ~15 Liters and a Kf<200. Assay yield=12.00 Kg (96.2%).

Step 4: Etherification

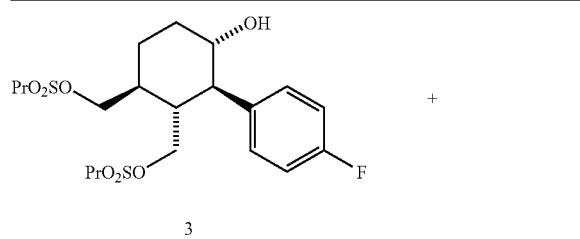

3

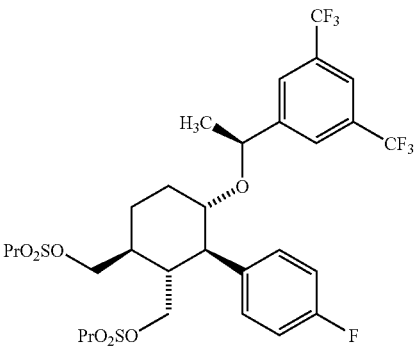

4 (1.6 equiv)

17 + 11% HBF₄, -16° C.
CH₂Cl₂/cyclohexane

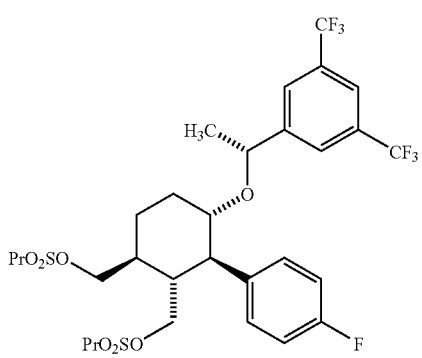

5

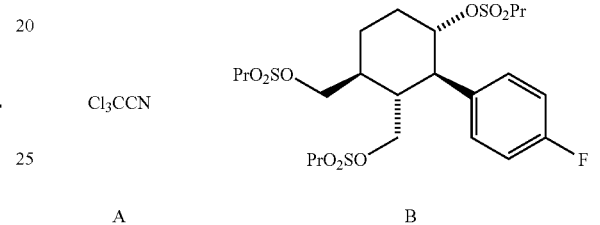

5a

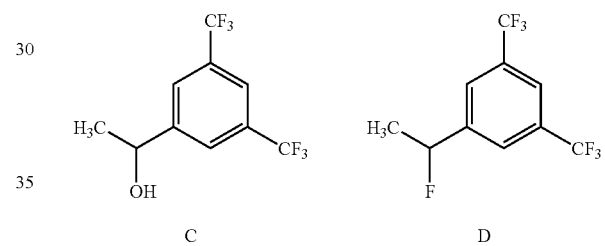

A      B

Cl₃CCN

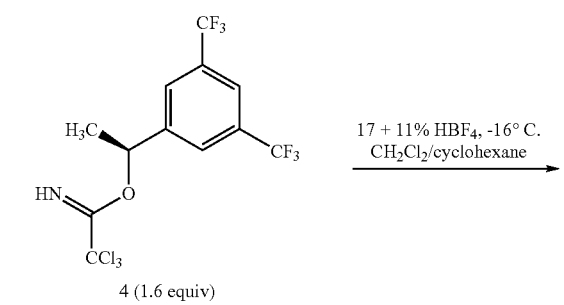

C      D

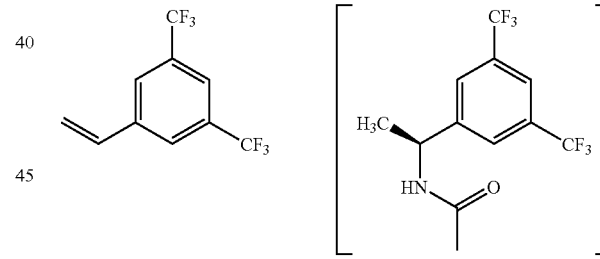

E      F (from MeCN quench)

|  | FW | mass | volume | mol | equiv. |
|---|---|---|---|---|---|
| Materials: | | | | | |
| Alcohol 3 | 466.58 | 6.73 kg | | 14.4 | 1.0 |
| Imidate 4 | 402.55 | 9.33 kg active | | 23.2 | 1.6 |
| HBF₄ (54 wt % in Et₂O) | 87.8 | | 0.558 L | 4.09 | 0.28 |
| cyclohexane | | | ~10 L | | |
| CH₂Cl₂ | | | ~9 L | | |
| NaOH | (2.0 N) | | 16 L | 32 | 2.2 |
| IPA | | | 125 L | | |

Procedure:

Charge the CH₂Cl₂ solution of the cyclohexanol 3 (containing 6.73 kg active 3+~0.78 kg of related other alcohols and ~6 L CH₂Cl₂, KF<250 ppm, equiv<1.2 mol % H₂O) to a 100 L extractor. Charge the imidate solution (~850 g/L in cyclohexane, ~11 L, containing ~2 L cyclohexane) followed by additional cyclohexane (8.0 L). The mixture turns cloudy due to 3 oiling out. Add more $CH_2Cl_2$ (2 L) to dissolve the oil. Cool to −17° C. (oiling out at ~0° C.) and add more $CH_2CL_2$ (1.3 L) to dissolve the oil. The KF at this point should be <110 ppm (<1.5 mol % water). Add 0.17 equiv of $HBF_4$ (0.339 L) in one portion, resulting in temperature rising to −16° C. The slightly cloudy mixture is aged at −16° C. It turns clear in ~40 min and a slurry starts to form and thickens as the reaction proceeds to generate poorly soluble trichloroacetamide A.

After aging at −16° C. for 18 hours, LC assay reveals ~82% conv and a 5/5a ratio of ~6. For slightly higher conversion, 0.11 equiv more $HBF_4$ (0.219 L) is added following by aging at −16° C. for 4 h. The reaction is then warmed to 5° C. and aged for 1 h before being quenched with NaOH (2 N, 16 L). The exotherm brings the temperature to 18° C. After aging at rt for ~15 min, the layers are allowed to settle. The bottom aqueous layer (~18 L) is cut away and the organic layer is washed with 18 L of water. The cloudy bottom organic layer is collected (assay yield of 5: ~74%), concentrated to ~20 L, and flushed with IPA (90 L) while keeping batch temperature at ~40° C. and volume at ~50-60 L to enable stirring as the product crystallizes out. A final volume of ~70 L is reached and the thick slurry is aged at rt until mother liquor shows<11 g/L loss (5/5a<0.55). The product is then filtered, washed with IPA (35 L), and dried. 7.07 kg, 98 A %, 96 wt %, 6.82 kg corrected, 67% yield.

Step 5: Cyclization with Allylamine

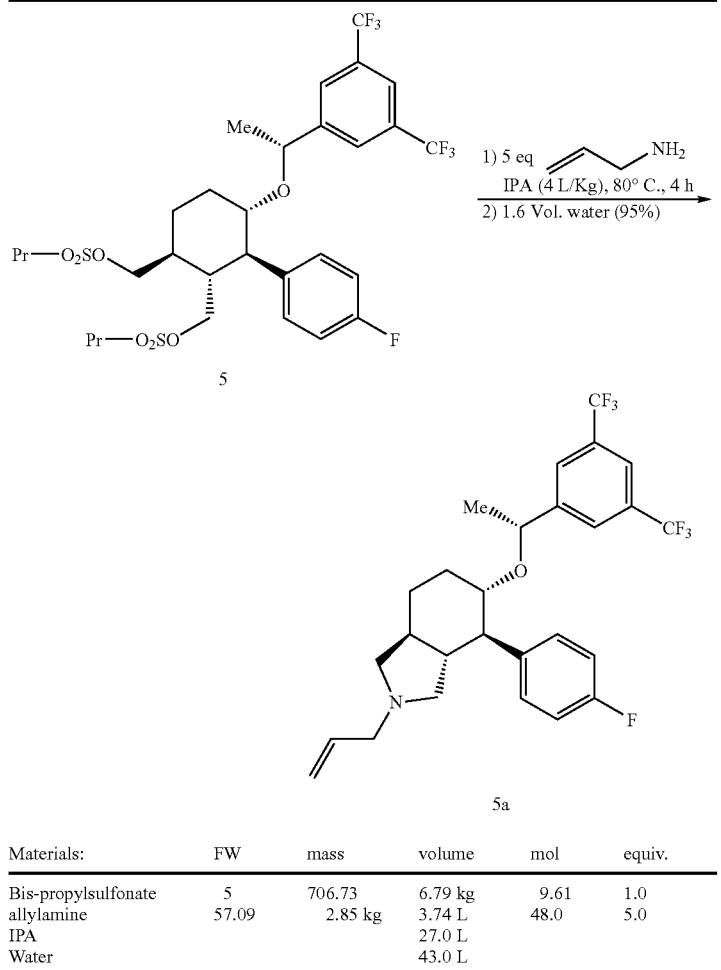

| Materials: | FW | mass | volume | mol | equiv. |
|---|---|---|---|---|---|
| Bis-propylsulfonate | 5 | 706.73 | 6.79 kg | 9.61 | 1.0 |
| allylamine | 57.09 | 2.85 kg | 3.74 L | 48.0 | 5.0 |
| IPA | | | 27.0 L | | |
| Water | | | 43.0 L | | |

Procedure

The reaction vessel was charged with IPA (27 L), allylamine (3.74 L, 50.0 moles), and bis-propylsulfonate (6.79 kg, 9.61 moles).

At room temperature, the mixture was a very thick (pasty) mixture that was difficult to stir. The reaction mixture loosens up upon heating and became completely homogeneous at +55-60° C. Note that allylamine was boiling at +53° C.

The mixture was heated to +75-80° C. for 4 h, and was cooled to +40° C. to room temperature. One half volume of water (13.5 L) was added and the batch was seeded (ca. 35 g, 0.5 wt %).

The batch may crystallize without seed but seeding gave more consistent results.

The batch was aged for 30 min and the remainder of water (29.5 L) was added over a couple hours. It was filtered, washed with 65/35 H2O/IPA (12 L). Product was dried at +40° C. for 24 hours under a stream of nitrogen to give 4.9 Kg of product (95% yield).

Step 6: Deprotection

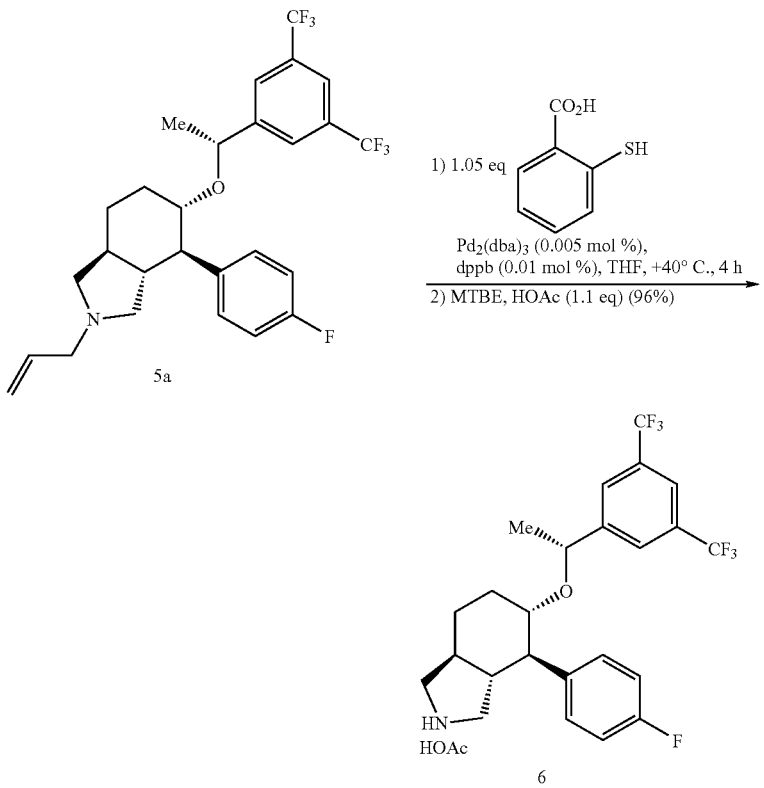

| Materials: | FW | mass | volume | mol | equiv. |
|---|---|---|---|---|---|
| Allyl-protected pyrrolide | 515.5 | | 5.16 kg | 10.0 | 1.0 |
| THF | | | 25.8 L | | |
| Thiosalicyclic acid | 154.2 | | 1.62 kg | 10.5 | 1.05 |
| Pd$_2$(dba)$_3$ | 915.7 | 46.0 g | | 0.005 | 0.005 |
| Dppb | 426.5 | 43.0 g | | 0.01 | 0.01 |
| MTBE | | | 41.0 L | | |
| NaOH | | | 25.8 L (1N) | 25.8 | |
| Water | | | 46.0 L | | |
| AcOH | 60.05 | 660 g | 629 mL | 11.0 | 1.1 |

Procedure

The reaction vessel was charged with THF (25.8 L), allylamine protected pyrrolidine (5.16 Kg, 10.0 moles), and thiosalicylic acid (1.62 Kg, 10.5 moles). The reaction mixture was degassed and dppb (4.3 g, 0.01 mol) was added followed by Pd$_2$(dba)$_3$ (4.6 g, 0.005 mol) under nitrogen. The mixture was stirred at +40° C. for 4 h, cooled to r.t and was reverse added into a stirred biphasic mixture made of MTBE (41 L) and 1 N aqueous NaOH solution (25.8 L). Layers were separated and the organic was washed with water (2×23 L). The organic solution was concentrated under vacuum with feeding of MTBE (in-line filtration w/1 μm) with a constant total volume of ca. 45 L to lower the KF to less than 5000 ppm.

THF at the end of distillation is ≦10 vol %.

The mixture (ca. 8-10 L MTBE/Kg) is heated to ca. +50° C. and acetic acid (10 Vol %, 62.9 mL) was added and the batch was seeded (0.1 wt %, 5 g) to initiate the crystallization. It was aged at +50° C. for 30 minutes and remaining acetic acid (535.5 mL) was added over ca. 1 h at +50° C.

The salt crystallizes as a quite thick slurry but remains stirrable. It loosens up upon aging. Alternatively, acetic acid can be added as an MTBE solution (ca. 1 M).

After aging at +50° C. for 2 h the batch was cooled to room temperature and aged for another 2 h, it was filtered, washed with MTBE (8 L) and dried at +40° C. under vacuum for 24 h to give 5.14 Kg of the product (96% yield). Pd was ca. 25 ppm.

Step 7: Preparation of Compound A

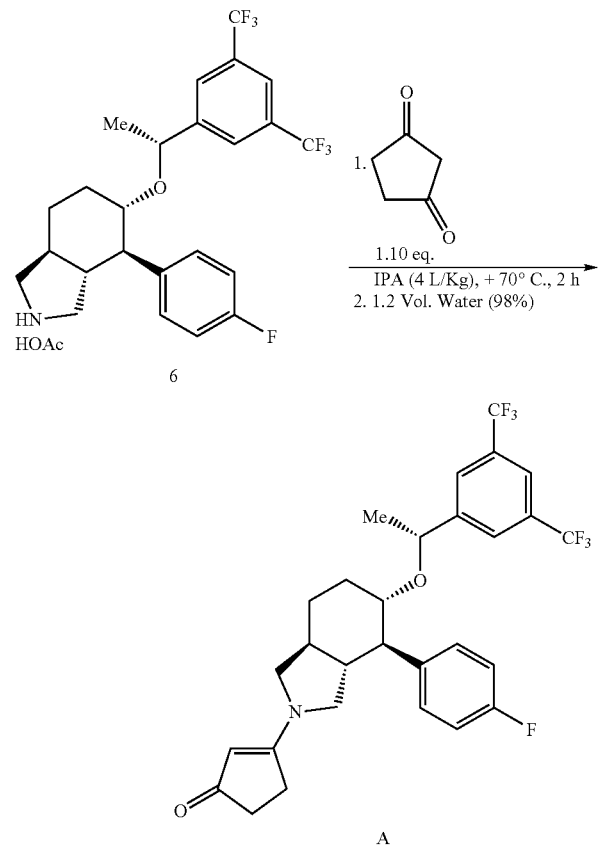

| Materials: | FW | mass | volume | mol | equiv. |
|---|---|---|---|---|---|
| Acetic acid Salt | 535.5 | 7.36 kg | | 13.74 | 1.0 |
| 1,3-cyclopentanedione | 98.10 | 1.48 kg | | 15.12 | 1.1 |
| IPA | | | 30 L | | |
| Water | | 36 L | | | |

A 100 liter flask was charged with IPA (26 L). To this was added the acetic acid salt (7.5 Kg) followed by 1,3-cyclopentanedione (1.51 Kg). The sides of the flask were washed with IPA (4 L) and the mixture is heated to +75° C. for 1 h at which point HPLC indicated that the reaction was complete. To the reaction mixture was then added ⅓ volume of water (10 L) keeping the temperature at +60° C. The batch was seeded (2.00 g, 0.02 wt %) to initiate crystallization. After aging at 50-60° C. for 30 min, the mixture was cooled to 40° C. The remaining water (26 L) was added over a period of 1.25 h and the slurry was aged for 12 hours at rt. The batch was filtered and the wet-cake was washed with 2 bed volumes of 2:1 Water/IPA and then 1 bed volume of water and dried overnight under vaccum/$N_2$sweep. The resulting wet cake was transferred to a vacuum over and further dried at 45° C. under vacuum with a sweep of nitrogen for 24 h to give 7.45 Kg of API (98% yield).

What is claimed is:

1. A process of making hydroisoindoline tachykinin receptor antagonists of Formula (I)

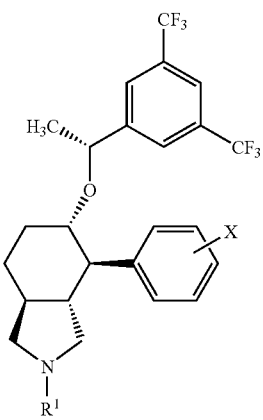

and pharmaceutically acceptable salts thereof, wherein
R1 is selected from the group consisting of
(1) hydrogen
(2) $C_{1-6}$alkyl, which is unsubstituted or substituted with halogen, hydroxyl or phenyl, (3) cyclopentenone, which is unsubstituted or substituted with halogen, hydroxyl or methyl,
(4) —(CO)—$C_{1-6}$alkyl,
(5) —(CO)—$NH_2$,
(6) —(CO)—$NHC_{1-6}$alkyl, and
(7) —(CO)—$N(C_{1-6}alkyl)(C_{1-6}alkyl)$;

X is independently selected from the group consisting of:
(1) hydrogen,
(2) fluorine, and
(3) methyl;

comprising:

Step (a) reacting a phenyl acetic acid of Formula (2)

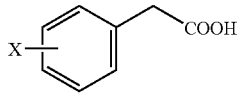
(2)

with $SOCl_2$ in an aprotic solvent optionally in the presence of a first catalyst to provide a compound of Formula (3)

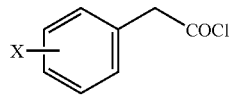
(3)

Step (b) reacting the compound of Formula (3) with NHMeOMe in the presence of an aqueous inorganic base to provide a Weinreb amide of Formula (4)

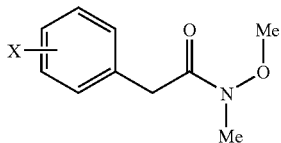
(4)

Step (c) reacting the Weinreb amid of Formula 4 with a suitable Grignard reagent in an second aprotic solvent followed by a first quenching with $Ac_2O$ and a second quenching with an aqueous inorganic acid to provide an enone of Formula (5)

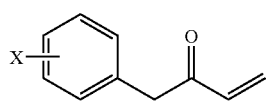
(5)

Step (d) reacting the enone of Formula (5) with a silane reagent in a third aprotic solvent and an organic base to provide a diene of Formula (6)

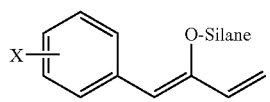
(6)

Step (e) reacting a diene of Formula (6) with a fumarate of Formula (7)

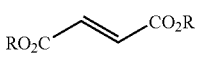
(7)

wherein R is (−)-menthyl and a Lewis acid in a non-polar solvent to provide a compound of Formula (8)

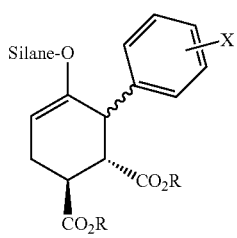
(8)

Step (f) hydrolyzing a compound of Formula (8) with suitable hydrolysis reagents in an organic polar solvent to provide a compound of Formula (9)

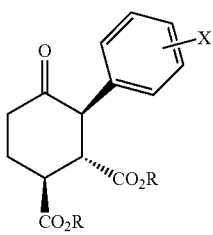
(9)

Step (g) reducing the ketone functionality of the compound of Formula (9) with a first reducing agent, followed by reduction of $CO_2R$ with a second reducing agent in an aprotic solvent to provide a triol of Formula (10)

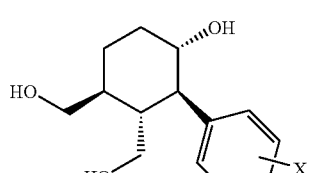
(10)

Step (h) reacting the triol of Formula (10) with an alkyl-sulfonyl chloride in the presence of an organic base to provide a compound of Formula (11)

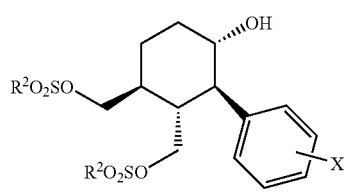
(11)

wherein R² is methyl, ethyl or propyl,

Step (i) reacting the compound of Formula (11) with compound of Formula (12)

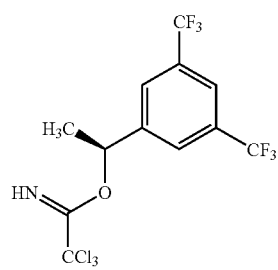
(12)

in the presence of an acid catalyst in an aprotic solvent to produce a compound of Formula (13)

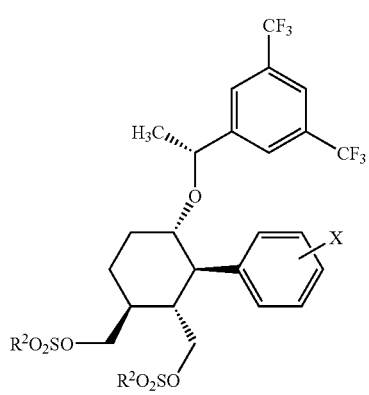
(13)

Step (j) cyclizing the compound of Formula (13) with allylamine in a polar solvent to provide a compound of Formula (14)

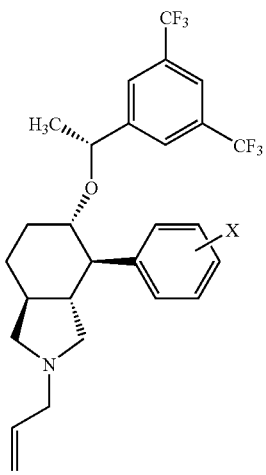
(14)

Step (k) reacting the compound of Formula (14) with third catalyst followed by addition of acid to provide a compound of Formula (15)

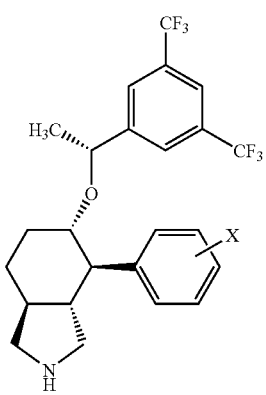
(15)

as an acid salt;

Step (l) reacting the acid salt of the compound of Formula (15) with a functionalizing reagent in a polar solvent to provide the compound of Formula (I)

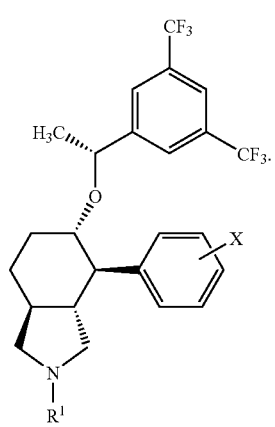
(I)

2. A process according to claim 1, wherein the compound of Formula (I) is

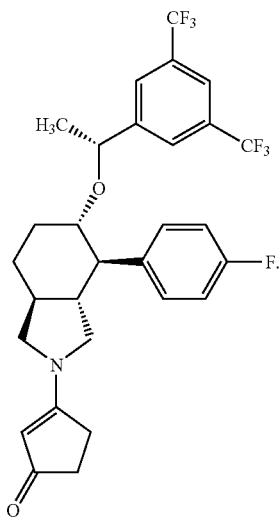

3. A process according to claim 1 wherein
Steps (a) and Step (b) is carried out in a single pot without intermediate isolation.
4. A process according to claim 1 wherein
in Step (a) the aprotic solvent is toluene or benzene; and the first catalyst is Di-methylformamide;
in Step (c) the second aprotic solvent is THF or Methyl-t-butyl ether or a mixture of toluene and THF;
the Grignard reagent is vinyl magnesium chloride or vinyl magnesium bromide;
in Step (d) the silane reagents is chlorotriethylsilane, chlorotrimethylsilane, or t-butyldimethylchlorosilane; the organic base is triethylamine, ethyldiisopropylamine, or DBU; the solvent is THF, MeCN, toluene, benzene or ether or a mixture thereof;
in Step (e), the Lewis acid catalysts is $Et_2AlCl$, $iBu_2AlCl$, or $EtAlCl_2$; the solvent is toluene, methylene chloride, 1,2-dichloroethane, or benzene;
in Step (f) the hydrolysis agents is aqueous HCl, HBr, HF, or HI; the solvent is MeCN or THF;
in Step (g) the first reducing agent is $LiAl(OtBu)_3H$ or $NaBH_4$; the second reducing agent is $LiAlH_4$ and $LiBH_4$; the solvent is THF or diglyme;
in Step (h), the alkanesulfony chlorides is propanesulfonyl chloride, ethanesulfonyl chloride, or methanesulfonyl chloride; the organic base is 2,4,6-collidine, ethyldiisopropylamine, tetramethylpiperidine, pentamethylpiperidine, 2,6-lutidine, or triethylamine; and wherein the reaction of Step (h) is carried out in a solvent selected from MeCN, THF, methylene chloride, EtOAc, iPrOAc and 1,2-dichloroethane;
in Step (i) the acid catalyst is $HBF_4$, $BF_3$, or $CF_3SO_3H$; the solvent is methylene chloride, 1,2-dichloroethane, toluene, trifluorotoluene, cyclohexane;
in Step (j) the solvent is 2-propanol, MeGH, EtOH or i-PrOAc;
the reaction of Step (k) is carried out in a solvent selected from THF or MTBL; and
in Step (l) the solvents is 2-propanol or toluene and the functionalizing reagent is an alkyl(aryl) halide, an alkyl(aryl) triflate, a dialkyl(aryl)carbonic anhydride, an acyl halide, an alkyl(aryl)chloroformate, alkyl(aryl)sulfonylhalide, a haloaklyl(aryl)sulfonylhalide, an alkanoyl halide, a benzylic halide, a halo-CON(alkyl or aryl)2, an alkyl(aryl) aldehyde or ketone in the presence of a reducing agent, or sulfonylate.

5. A process of making a compound of Formula (I)

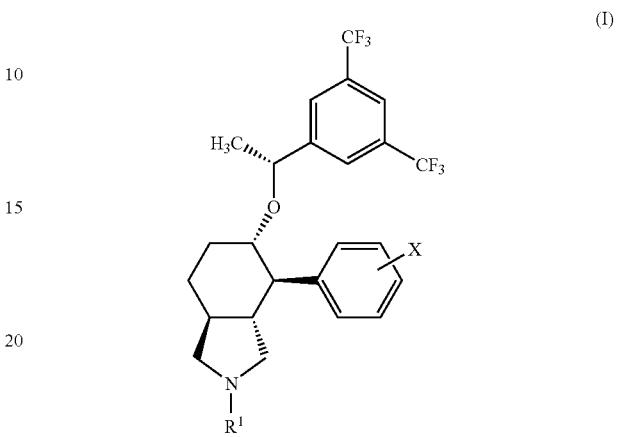

and pharmaceutically acceptable salts thereof, wherein
R1 is selected from the group consisting of
(1) hydrogen
(2) $C_{1-6}$alkyl, which is unsubstituted or substituted with halogen, hydroxyl or phenyl,
(3) cyclopentenone, which is unsubstituted or substituted with halogen, hydroxyl or methyl,
(4) —(CO)—$C_{1-6}$alkyl,
(5) —(CO)—$NH_2$,
(6) —(CO)—$NHC_{1-6}$alkyl, and
(7) —(CO)—$N(C_{1-6}$alkyl)($C_{1-6}$alkyl);
X is independently selected from the group consisting of:
(1) hydrogen,
(2) fluorine, and
(3) methyl;
comprising
Step (k) reacting the compound of Formula (14)

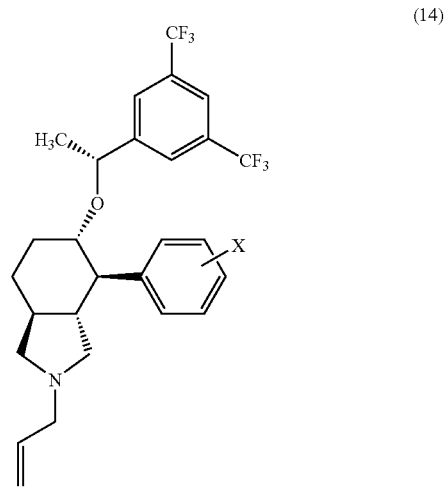

with third catalyst followed by addition of acid to provide a compound of Formula (15)

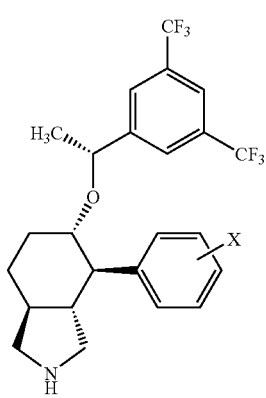
(15)

as an acid salt; and

Step (l) reacting the acid salt of the compound of Formula (15) with a functionalizing reagent in a polar solvent to provide the compound of Formula (I).

6. A process according to claim 5, wherein the compound of Formula (I) is

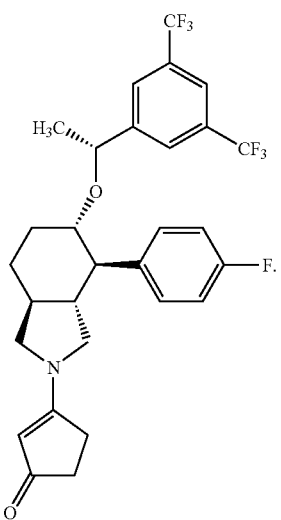

7. A process according to claim 5 comprising

Step (j) cyclizing the compound of Formula (13)

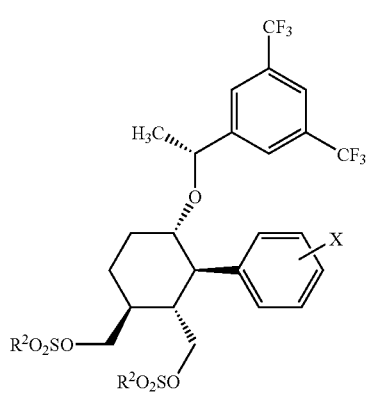
(13)

wherein $R^2$ is methyl, ethyl or propyl, with allylamine in a polar solvent to provide a compound of Formula (14)

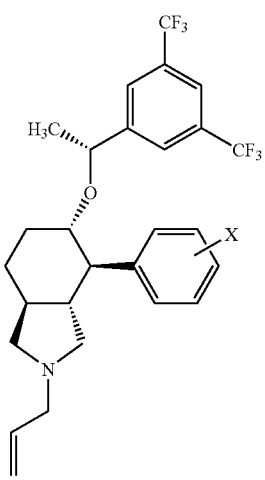
(14)

Step (k) reacting the compound of Formula (14) with third catalyst followed by addition of acid to provide a compound of Formula (15)

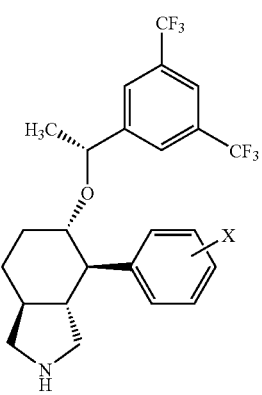
(15)

as an acid salt;

Step (l) reacting the acid salt of the compound of Formula (15) with a functionalizing reagent in a polar solvent to provide the compound of Formula (I).

8. A process according to claim 7 comprising

Step (i) reacting the compound of Formula (11)

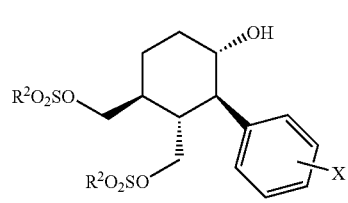
(11)

with compound of Formula (12)

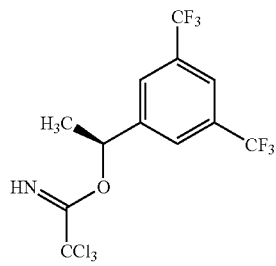

in the presence of a acid catalyst in a aprotic solvent to produce a compound of Formula (13)

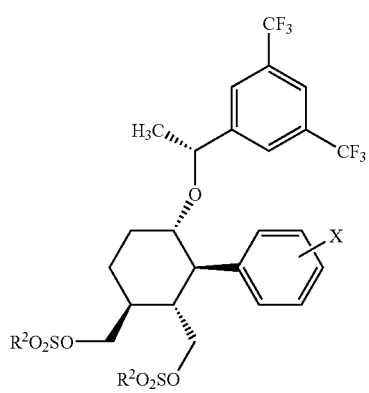

Step (j) cyclizing the compound of Formula (13) with allylarnine in a polar solvent to provide a compound of Formula (14)

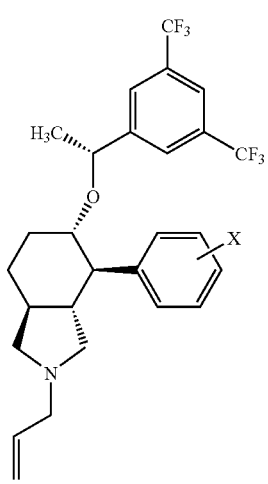

Step (k) reacting the compound of Formula (14) with third catalyst followed by addition of acid to provide a compound of Formula (15)

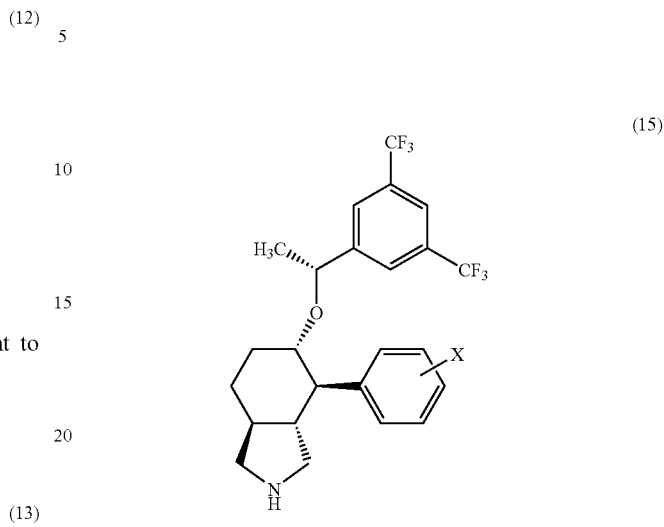

as an acid salt;

Step (l) reacting the acid salt of the compound of Formula (15) with a functionalizing reagent in a polar solvent to provide the compound of Formula (I).

9. A process according to claim 8 wherein
in Step (i) the acid catalyst is $HBF_4$, $BF_3$, or $CF_3SO_3H$; the solvent is methylene chloride, 1,2-dichloroethane, toluene, trifluorotoluene, cyclohexane;
in Step (j) the solvent is 2-propanol, MeGH, EtOH or i-PrOAc;
the reaction of Step (k) is carried out in a solvent selected from THF or MTBE; and
in Step (l) the solvents is 2-propanol or toluene.

10. A process of making a compound of Formula 13

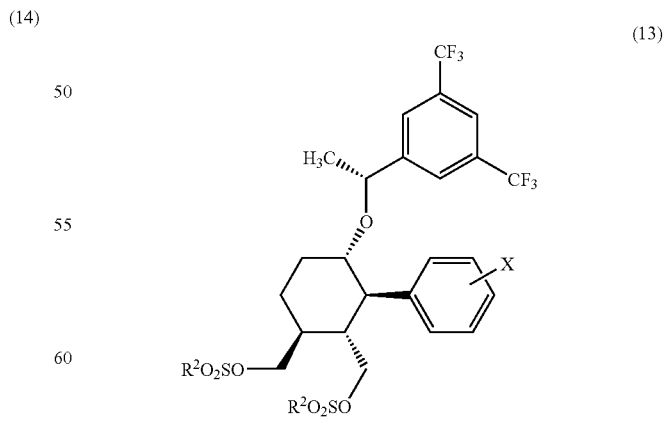

wherein $R^2$ is methyl, ethyl or propyl,

Step (i) reacting the compound of Formula (11)

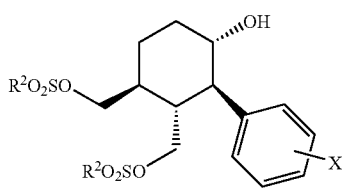
(11)

with compound of Formula (12)

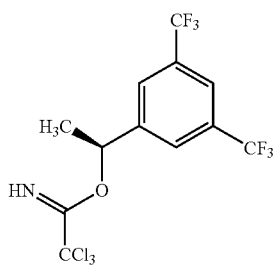
(12)

in the presence of an acid catalyst in an aprotic solvent to produce a compound of Formula (13).

11. A process according to claim 10 wherein $R^2$ is propyl, the acid catalyst is $HBF_4$, $BF_3$, or $CF_3SO_3H$; and the solvent is methylene chloride, 1,2-dichloroethane, toluene, trifluorotoluene or cyclohexane.

12. A process of making a compound of Formula 14

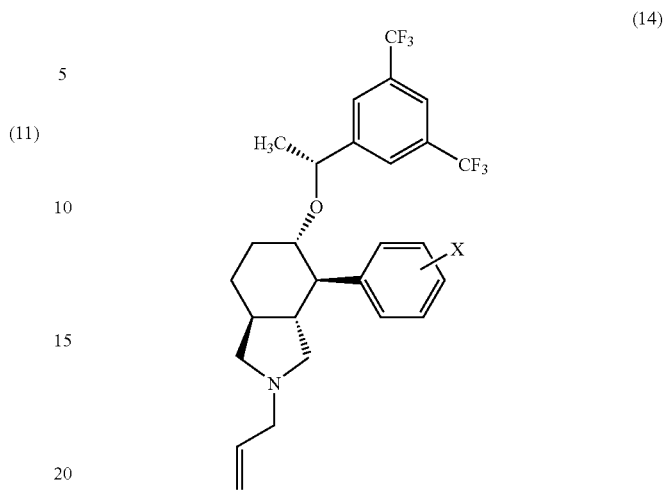
(14)

comprising:
Step (j) cyclizing the compound of Formula (13)

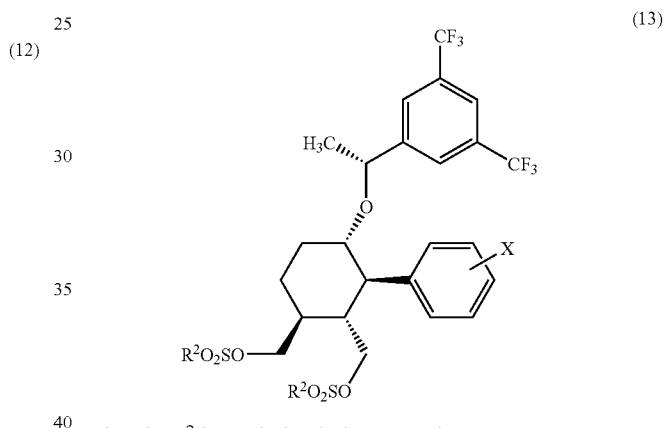
(13)

wherein $R^2$ is methyl, ethyl or propyl,
with ailylamine in a polar solvent to provide a compound of Formula (14).

13. A process according to claim 12 wherein
$R^2$ is propyl, and
in Step (j) the solvent is 2-propanol, MeOH, EtOH or i-PrOAc.

* * * * *